(12) United States Patent
Baughman et al.

(10) Patent No.: US 8,269,042 B2
(45) Date of Patent: Sep. 18, 2012

(54) CRYSTALLIZED DIACETYLENIC INDICATOR COMPOUNDS AND METHODS OF PREPARING THE COMPOUNDS

(75) Inventors: Ray H. Baughman, Dallas, TX (US); Lee J. Hall, Irving, TX (US); Mikhail Kozlov, Dallas, TX (US); Dawn E. Smith, Martinsville, NJ (US); Thaddeus Prusik, Stroudsburg, PA (US)

(73) Assignee: Temptime Corporation, Morris Plains, NJ (US)

( * ) Notice: Subject to any disclaimer, the term of this patent is extended or adjusted under 35 U.S.C. 154(b) by 693 days.

(21) Appl. No.: 12/261,887

(22) Filed: Oct. 30, 2008

(65) Prior Publication Data

US 2009/0131718 A1 May 21, 2009

Related U.S. Application Data

(60) Provisional application No. 60/983,828, filed on Oct. 30, 2007.

(51) Int. Cl.
  *C07C 275/04* (2006.01)
(52) U.S. Cl. ......................................... 564/63
(58) Field of Classification Search ........................ None
  See application file for complete search history.

(56) References Cited

U.S. PATENT DOCUMENTS

| | | | |
|---|---|---|---|
| 3,999,946 A | 12/1976 | Patel et al. | |
| 4,189,399 A | 2/1980 | Patel | |
| 4,220,747 A | 9/1980 | Preziosi et al. | |
| 4,384,980 A | 5/1983 | Patel | |
| 4,536,450 A | 8/1985 | Garito | |
| 4,788,151 A | 11/1988 | Preziosi et al. | |
| 4,788,432 A * | 11/1988 | Patel | 250/472.1 |
| 4,789,637 A | 12/1988 | Preziosi et al. | |
| 5,709,472 A * | 1/1998 | Prusik et al. | 374/106 |
| 6,924,148 B2 | 8/2005 | Prusik | |
| 7,019,171 B1 | 3/2006 | Prusik et al. | |
| 2008/0004372 A1 | 1/2008 | Prusik et al. | |

FOREIGN PATENT DOCUMENTS

| | | | |
|---|---|---|---|
| CA | 1237145 | * | 5/1988 |
| EP | 0 149 784 | | 7/1985 |
| WO | WO2004/077097 | | 9/2004 |

OTHER PUBLICATIONS

Burke "Solubility Parameters: Theory and Application" The Book and Paper Group Annual, vol. 3, 1984, The American Institute for Conservation of Historic and Artistic Works (AIC).
International Search Report and Written Opinion for International Patent Application No. PCT/US08/81835 dated Jan. 29, 2009.
Enkelmann "Polymerization in Mixed Crystals", J. Materials Science, 15 (1980) pp. 951-958.
Enkelmann "The Solid-State Polymerization, Physical Properties, and Crystal Structures of Diacetylene Mixed Crystals" Makromol. Chem. 184, 1945-1955 (1983).

(Continued)

*Primary Examiner* — Yate K Cutliff
(74) *Attorney, Agent, or Firm* — K&L Gates LLP

(57) ABSTRACT

Crystallized diacetylenic compounds having certain crystallographic and other characteristics; diacetylenic compounds and mixtures crystallized from diacetylenic solutions; methods of preparing and identifying solvent systems for dissolving diacetylenic compounds; diacetylenic solutions; methods of recrystallizing diacetylenic compounds; crystals of 2,4-hexadiyn-1,6-bis(alkylurea) compounds; and ambient condition indicators and time-temperature condition indicators comprising crystallized diacetylenic compounds.

20 Claims, 14 Drawing Sheets

OTHER PUBLICATIONS

Hansen, C. M., Solubility Parameters: A user's handbook, 2000, CRC, p. 77, p. 80, p. 82-83.

Brandrup, J., Eds. in Polymer Handbook, 4th ed.; John Wiley & Sons, Inc. Hoboken, NJ; 1999, vol. 2 (method of van Krevelyn), p. 682-683, p. 686.

Baughman et al., "Solid-State Polymerization of Linear and Cyclic Acetylenes", Journal of Polymer Science: Macromolecular Reviews, 1978, vol. 13, pp. 219-239.

Baughman et al., "Theory of single-phase solid-state polymerization reactions", J. Chem. Phys., 73(8), 1980, pp. 4113-4125.

Baughman et al., "Solid-state reactions kinetics in single-phase polymerizations", J. Chem. Phys., 68(7), 1978, pp. 3110-2121.

Baughman et al., "Solid-State Synthesis of Large Polymer Single Crystal", Journal of Polymer Science: Polymer Physics Edition, 1974, vol. 12, pp. 1511-1535.

Wegner et al. "Topochemical Reactions of Monomers with Conjugated Triple Bonds" J. Poly. Sci.B.Poly. Letters vol. 9 (1971), pp. 133-144.

Wegner, "Topochemical Polymerization of Monomers with Conjugated Triple Bonds" Die Makromoleculare Chemie 154 (1972) pp. 35-48.

S.L. Morissette, et al. "Elucidation of crystal form diversity of the HIV protease inhibitor ritonavir by high-throughput crystallization", PNAS, 2003, vol. 100, No. 5, pp. 2180-2184, www.pnas.org/cgi/doi/10.1073/pnas.0437744100.

Terada, et al. Determination of solubility parameters for poly(3-hydroxyalkanoates), International Journal of Biological Macromolecules, 25 (1999), pp. 207-215.

Dautel, et al. "Self-Organized Ureido Substituted Diacetylenic Organogel. Photopolymerization of One-Dimensional Supramolecular Assemblies to Give Conjugated Nanofibers", J. Am. Chem. Soc. 2006, 128, pp. 16213-16223.

Dautel, et al. "Self-Organized Ureido Substituted Diacetylenic Organogel. Photopolymerization of One-Dimensional Supramolecular Assemblies to Give Conjugated Nanofibers", Supporting Information, S1-S19, J. Am. Chem. Soc. 2006, 128, pp. S1-S19.

* cited by examiner

CRYSTALLIZED DIACETYLENIC INDICATOR COMPOUNDS AND METHODS OF PREPARING THE COMPOUNDS

CROSS-REFERENCE TO A RELATED APPLICATION

This application claims the priority of provisional patent Application No. 60/983,828 filed Oct. 30, 2007 the entire disclosure of which is incorporated by reference herein.

STATEMENT REGARDING FEDERALLY SPONSORED RESEARCH OR DEVELOPMENT (Not applicable.)

The present invention relates to new crystallized diacetylenic compounds and to methods of preparing the compounds. The herein described methods and products are generally useful in relation to diacetylenic compounds, or monomers, employable as active agents in visual indicators of exposure to environmental conditions, for example conditions such as temperature that relate to the shelf life, freshness, maturity or other characteristic of a host product.

BACKGROUND

Various diacetylenic monomers that undergo a solid-state polymerization reaction giving rise to color development, or another visually apparent change, in a predictable and irreversible manner, have long been used as active agents in time-temperature and other ambient condition indicators. Such indicators can provide a simple visual indication of the cumulative exposure of a host product to an environmental condition. They may be used to monitor the useful shelf life of perishable host products such as a foodstuff, vaccine, medicament or the like, which can be adversely affected by inappropriate ambient temperatures or other conditions of their surroundings or storage environment. The indicator system can comprise a label incorporating the diacetylenic monomer as an active agent. The label can be affixed to the host product or to its packaging or otherwise associated with the host product, or can be embodied in some other convenient form.

In the polymerization reaction, many diacetylenic molecules are chained together to form a polydiacetylene. This reaction takes place in the solid state and is irreversible. In some cases, colorless or nearly colorless crystals of the diacetylenic compound, a monomer in this context, transform into intensely colored crystals of polymer in response to sufficient cumulative exposure to heat or another environmental condition. The polymerization reaction proceeds spontaneously, at rates largely determined by the ambient conditions.

The color change resulting from the polymerization reaction is irreversible. This property makes the compounds useful for monitoring perishable products such as food or medicines that may lose freshness after excessive cumulative exposure to heat. Diacetylenic monomers can also be employed as the active agents in indicators used for monitoring the maturity of maturing products, for example wine or cheese. For these and other purposes, the diacetylenic monomer can be incorporated as the active agent in an indicator label to be associated with a host product to be monitored. The indicator label provides a color change, derived from polymerization of the diacetylenic monomer, which can be perceived by a human viewer at a convenient viewing distance, for example by a shopper inspecting a refrigerated display in a supermarket. A reversible indicator would not be useful for these purposes.

In order to effectively track possible changes in the host product it can be desirable for the diacetylenic monomer employed to have response parameters to heat, or to another ambient condition being monitored, that may approximately correlate with the response parameters the intended host product has to the same ambient or environmental condition. For this purpose, it would be useful for the indicator formulator to have a wide range of commercially useful diacetylenic monomers providing a variety of response parameters from which to choose a suitable monomer for monitoring a particular host product.

Many polymerizable diacetylenic compounds are known or have been suggested, some of which provide useful color changes upon polymerization, see for example Patel U.S. Pat. Nos. 3,999,946; 4,189,399 and 4,384,980 and Preziosi et al. U.S. Pat. Nos. 4,789,637 and 4,788,151. However, only a limited number of these compounds exhibit performance parameters that render them useful for monitoring a perishable or maturing commercial product. The limited number of useful diacetylenic compounds that is commercially available restricts the choice of response parameters an indicator formulator has when seeking a diacetylenic monomer to use as an active indicator agent.

Accordingly, the art includes proposals for modifying the reactivity of a given commercially useful diacetylenic monomer so that it responds differently to a given ambient condition, so as to give the formulator more choices.

For example, U.S. Pat. No. 4,788,151 to Preziosi et al. discloses dissolving two or more diacetylenic compounds in a heated common solvent and recrystallizing the solvated compounds to produce a co-crystallized composition. The co-crystallized composition has a reactivity different from that of the individual compounds.

International Publication No. WO 2004/077097 to JP Laboratories discloses radiation sensitive devices, such as a film, sticker or badge for monitoring a dose of high-energy radiations utilizing radiation sensitive materials, such as diacetylenes. As described in WO 2004/077097, diacetylenes are known to crystallize into more than one crystallographic modification or phase, and by selecting a proper solvent system, some diacetylenes, can be crystallized into a phase which would have extremely low thermal reactivity and a high radiation reactivity.

Also, Prusik et al. U.S. Pat. No. 6,924,148 discloses refluxing a solution of an acetylenic agent to vary its reactivity. Some examples in the patent describe the use of glacial acetic acid and dimethyl formamide as solvents for the purpose. A number of other solvents are also disclosed as employable in the practice of the described invention. However, specific information regarding the solubilities of diacetylenic compounds in such other solvents does not appear to be provided. Some X-ray diffraction data are provided for one diacetylenic monomer compound.

Furthermore, U.S. Pat. No. 7,019,171 to Prusik et al. discloses non-comminutive processes for favorably influencing particle size in acetylenic agent crystallization processes. Some described examples employ solutions of acetylenic agents in acetic acid and various solvents such as aqueous methanol and ethyl 3-ethoxypropionate are described as useful as a precipitation or quenching fluid.

In addition, U.S. Patent Publication No. 2008/0004372 (application Ser. No. 11/427,589) to Prusik et al. discloses use of a reactivity-enhancing adjuvant to adapt the reactivity of a diacetylenic indicator agent.

Notwithstanding the various known diacetylenic monomers and methods of providing diacetylenic monomers with modified reactivities, it would be desirable to have more diacetylenic monomer reactivity options available, and to have new methods and products for providing diacetylenic monomers with new or modified reactivities.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

SUMMARY OF THE INVENTION

The present invention provides, inter alia, crystallized diacetylenic compounds in a new or modified reactivity state. The crystallized diacetylenic compound can be one or more compounds which provide an irreversible appearance change in an environmental condition indicator, for example a cumulative time-temperature indicator. The appearance change can, for example, be a change in color, intensity or darkness of the appearance of the compound or compounds.

The invention also provides methods of preparing crystallized diacetylenic compounds and solvent systems and diacetylenic solutions useful in these methods.

In one aspect the invention provides a crystallized diacetylenic compound capable of providing an irreversible appearance change in an environmental condition indicator, the crystallized diacetylenic compound having a crystal structure comprising a polymerizable diacetylenic monomer of structural formula

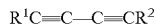

wherein each of $R^1$ and $R^2$ independently is an organic substituent compatible with providing the irreversible appearance change. The polymerizable diacetylenic monomer molecules can have a center-to-center separation, referring to the geometric centers of adjacent unit cells of the crystal, of less than 4.7 Å, the center-to-center separation being in a direction wherein solid-state polymerization can occur. The center-to-center separation can correspond to a unit cell repeat distance of the crystallized diacetylenic compound.

Each of $R^1$ and $R^2$ independently can be —$R^4$NHCONHR$^3$ where $R^3$ is alkyl having from 1 to 20 carbon atoms, optionally ethyl, propyl, butyl, octyl, dodecyl or octadecyl and $R^4$ is alkyl having from 1 to 20 carbon atoms. Alternatively, each of $R^1$ and $R^2$ independently can be —$CH_2$NHCONHR$^3$ where $R^3$ is alkyl, optionally ethyl, propyl, butyl, octyl, dodecyl or octadecyl.

Where $R^1$ and $R^2$ each comprise a —NHCONH— group, the crystallized diacetylenic compound can comprise two hydrogen bonds for each urea group, each one of the two hydrogen bonds extending between one of the two NH groups on one polymerizable diacetylenic molecule and a C=O group in a neighboring polymerizable diacetylenic molecule.

If desired, the polymerizable diacetylenic monomer can be symmetrically substituted and optionally can have a crystal structure wherein the diacetylene compound has a center of symmetry and no axes or planes of symmetry exist. The structure of a crystal having no axes or planes of symmetry is generally described as "triclinic".

The crystallized diacetylenic compound agent can optionally comprise at least one non-acetylenic compound in the crystal phase, the at least one non-acetylenic compound optionally being a solvent or solvents. As stated, the crystallized diacetylenic compound, or monomer, can polymerize to provide an indicator response, for example a color change, in response to ambient heat. Desirably, the crystallized diacetylenic compound comprises not more than about 10 percent by weight, of the polymerized diacetylenic compound based upon the weight of the diacetylenic compound and the polymer. The proportion of polymer can for example be not more than about 3 percent or not more than about 1 percent or lower.

The invention also provides, in a further aspect, a crystallized diacetylenic compound having a crystal size in a first direction of greater than about 100 microns and a maximum dimension in a second direction perpendicular to the first direction of not more than about 10 microns.

In another aspect the invention provides a crystallized diacetylenic compound having the structural formula

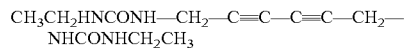

and having a triclinic crystal structure. The compound can have a centrosymmetric crystal phase wherein the centrosymmetric crystal phase has unit cell parameters of a=about 4.2 Å, b=about 4.6 Å, c=about 16.5 Å, α=about 89° β=about 85°, and γ=about 81°.

The invention also provides, in a further aspect, a crystal of a 2,4-hexadiyn-1,6-bis(alkylurea) compound exhibiting an X-ray diffraction pattern comprising two high intensity peaks at low 2θ diffraction angles of less than about 15 degrees. The diffraction pattern also comprises less than four high intensity peaks at high 2θ diffraction angles in the range of from about 19 degrees to about 24 degrees, when characterized using X-ray at a wavelength of about 1.54 Å. In one embodiment of this aspect of the invention, the X-ray diffraction pattern comprises no high intensity peaks at high 2θ diffraction angles in the range of from about 19 degrees to about 24 deg.

The 2,4-hexadiyn-1,6-bis(alkylurea) compound can, for example, be 2,4-hexadiyn-1,6-bis(propylurea) or 2,4-hexadiyn-1,6-bis(ethylurea) and can be recrystallized from a solution of 2,4-hexadiyn-1,6-bis(propylurea) or 2,4-hexadiyn-1,6-bis(ethylurea), respectively, in a mixture of water with ethyl alcohol, with isopropyl alcohol, with dimethyl sulfoxide or with another suitable solvent.

In addition, the invention provides, in a still further aspect, a crystal of a 2,4-hexadiyn-1,6-bis(alkylurea) compound recrystallized from a solvent system, the crystal exhibiting an X-ray diffraction pattern comprising two high intensity peaks at low 2θ diffraction angles of less than 12 degrees and comprising no more than four high intensity peaks at high 2θ diffraction angles in the range of from about 19 degrees to about 24 degrees wherein the high angle diffraction pattern is determined by the solvent system employed for recrystallization.

Crystallized diacetylenic compounds according to the invention can have a relatively high purity, for example being at least about 99.8 percent by weight pure, or can be less pure, for example being at least about 90 percent by weight pure.

Crystallized diacetylenic compounds according to the invention can be prepared by any suitable method, for example by crystallizing the diacetylenic compound from a diacetylenic solution of the diacetylenic compound in a solvent system.

If desired, the diacetylenic solution can be prepared by dissolving the diacetylenic compound in the solvent system and the diacetylenic compound, optionally, can comprise an unpurified crystallization product.

The invention also includes an ambient condition indicator, optionally a time-temperature indicator or a high energy radiation monitor, which comprises a crystallized diacetylenic compound, or a crystallized diacetylenic agent as described herein, the at least one crystallized diacetylenic compound or agent providing a visual appearance change in response to exposure to an ambient condition.

In another aspect, the invention provides a time-temperature indicator comprising a solid phase composition including a diacetylene having the structural formula

the diacetylene being capable of polymerizing by a reaction between molecules of the diacetylene wherein a C═O group on one molecule hydrogen bonds to two NH groups on an adjacent molecule and wherein:

"m" is an odd number from 1 to 7;
"n" is an odd number from 1 to 19; and
the solid phase comprises a triclinic space group P-1.

In an alternative aspect of the invention "n" is an even number from 2 to 20 rather than an odd number and the solid phase comprises a monoclinic space group $P2_1/a$ or $P2_1/c$ wherein the b axis is the $2_1$ axis rather than a triclinic space group P-1.

In some embodiments of the invention, the solvent system has a polar solubility parameter in the range of from about 6 $MPa^{1/2}$ to about 17 $MPa^{1/2}$ and has a hydrogen bond solubility parameter in the range of from about 7.5 $MPa^{1/2}$ to about 26 $MPa^{1/2}$, provided that the solvent system does not consist of acetic acid, dimethyl formamide or pyridine as the sole component of the solvent system.

By choosing solvents with the solubility parameters specified, new and useful solvent systems for diacetylenic monomers can be identified and the available range of solvent systems providing a desired diacetylenic solubility can be increased.

By identifying a new crystal phase or form for a given diacetylenic monomer the invention can enable the scope of potential commercial applications for the diacetylenic monomer to be expanded. In some instances a new crystal phase or form can provide a new set of time-temperature parameters for reaction, providing a correspondingly increased ability to match the time-temperature characteristics for the degradation of perishable products or the desired degree of maturation for maturing products.

The invention also provides, in additional aspects, methods useful for identification of one or more new solvent systems for a diacetylenic compound which solvent systems have novel combinations of properties such as ability to solubilize one or more useful diacetylenic compounds, environmental compatibility properties or useful combinations of these or other properties.

The invention also provides various methods of preparing a diacetylenic solution. One method comprises devising a solubility map depicting solvents by their solubility parameters and using the solubility map to identify and select prospective solvent components of a solvent system for a diacetylenic monomer to be dissolved. Another method comprises dissolving a diacetylenic compound or diacetylenic compounds in one of the novel solvent systems disclosed herein wherein the dissolved diacetylenic compound or diacetylenic compounds comprise or comprises the raw product of crystallization from a synthesis mixture, or from the product of methanol precipitation from a hot acetic acid solution.

Some surprising solvent mixtures are provided by the invention, in which a polymerizable diacetylenic compound has a solubility which is markedly higher than its solubilities in either of the individual solvents. These and other newly discovered solubility options enable diacetylenic compounds to be recrystallized in new ways, in some cases providing new reactivity choices.

BRIEF DESCRIPTION OF THE SEVERAL VIEWS OF THE DRAWING

Some embodiments of the invention, and of making and using the invention, as well as the best mode contemplated of carrying out the invention, are described in detail herein, by way of example, with reference to the accompanying drawings, in which like reference characters designate like elements throughout the several views, and in which.

Figure 1:
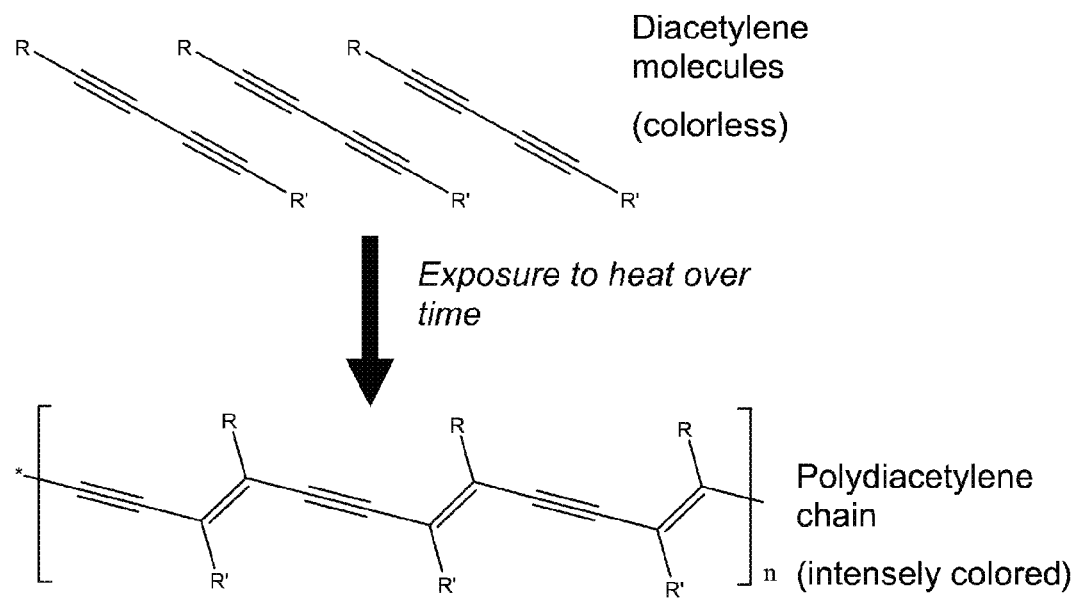
FIG. 1 is a simplified schematic diagram of one model of diacetylene polymerization.

Other examples of the practice of the invention will be or become apparent to a person of ordinary skill in the art in light of this disclosure.

DETAILED DESCRIPTION OF THE INVENTION

The present invention provides, inter alia, crystallized diacetylenic compounds, sometimes referenced as "monomers" herein, crystals comprising or consisting of diacetylenic compounds, also referenced as "diacetylenes" herein, and diacetylenic compositions which have new reactivities, or which provide more reactivity choices. In general, the diacetylenic materials provided by the invention can be prepared by physical processing, or physical modification, of known diacetylenic compounds without chemical change or modification of the starting material, or changing the chemical structure of the starting material.

To facilitate physical processing and reactivity modification the invention also provides new solvents and solvent systems for diacetylenic monomers including solvents in which one or more diacetylenic monomers has good room-temperature solubility. The invention includes solutions of diacetylenic monomers dissolved in the new solvents.

Also the invention provides quantitative information regarding diacetylenic monomer solubility in such new solvents. Other aspects of the invention provide new diacetylenic monomer crystals and crystal structure information which can be derived by recrystallization from the new diacetylenic monomer solutions.

The invention includes methods of preparing solvent systems, methods of recrystallization, methods of determining useful crystal structure information as well as diacetylenic indicator solutions and molecular modeling methods.

The invention includes a diacetylenic compound crystallized from the diacetylenic solutions described herein or prepared by a method as described herein. The invention also includes a mixture of diacetylenic compounds crystallized from the diacetylenic solution wherein the mixture comprises a crystal phase and wherein the crystal phase comprises two or more diacetylenic compounds.

The invention further includes methods of making an environmental condition indicator comprising applying the diacetylenic solution to a substrate.

Many solvents have been suggested as being useful for dissolving diacetylenes in general. However, little solubility data exists as to the particular solubility of a given diacetylenic compound in a specific solvent. While some diacetylenic compounds may show some solubility in a suggested solvent, the solubility may be quite low and less than would be useful for further processing. Many diacetylenic compounds have little known solubility at room temperature and may be processed at elevated temperatures. For example, some diacetylenic monomers are recrystallized from hot glacial acetic acid at temperatures of the order of 90-100° C.

Diacetylenic compounds for monitoring thermally unstable perishables are generally expensive to make and store. Room-temperature reactive diacetylenic compounds, which are useful for a number of purposes including freshness indicators, are expensive to store, sometimes requiring refrigeration at low temperatures. These and other considerations make it difficult to conduct large-scale screening tests to identify potentially useful new solubility properties of diacetylenic compounds.

Accordingly, the invention provides a method of identifying prospective solvents, having useful diacetylenic solubility, which can reduce or avoid the need for wholesale screening of solvents. In some embodiments, the methods enable a specific solubility, for example at least 1 percent or at least 4 percent by weight of the solution, to be provided.

The present invention employs new understandings and insights regarding certain diacetylenic compounds, or monomers, and provides means to manipulate their indicator-related reactivity, and other properties, through changes in physical processing which leave the compounds unchanged chemically. The invention includes embodiments which can provide new reactivity characteristics without modifying the diacetylenic monomer via chemical reactions. This is because new molecules that are chemically differentiated from established commercial products could require expensive studies for safety and other purposes for some applications. Accordingly, the invention provides, in some aspects, crystallized diacetylenic compounds in new or modified physical states which have new or modified reactivities as compared with compounds of chemically identical structure. For example, the diacetylenic compounds may have a particular crystal structure.

To lead to new reactivities or other properties it would be desirable to more fully understand the structure of diacetylenic monomers and their mechanisms of reaction at the molecular level. The invention also provides new methods and products helpful to these ends.

While the invention is not limited by any particular theory, in the solid state polymerization of a diacetylenic compound, a "monomer" or "diacetylenic monomer" in the context of polymerization, it is believed to be the crystal structure of the monomer which holds the individual diacetylenic monomer molecules juxtaposed in a manner enabling spontaneous polymerization. This concept is illustrated in FIG. 1 where three diacetylenic monomer molecules are shown arrayed in parallel alignment, in a longitudinally and angularly ordered manner, as they might be disposed in a solid crystal of the diacetylenic monomer. The acetylenic groups of adjacent molecules are in sufficient proximity that they can spontaneously form double bonds between adjacent molecules to link the monomer molecules together into the 1-4 addition polymer product.

Figure 2:
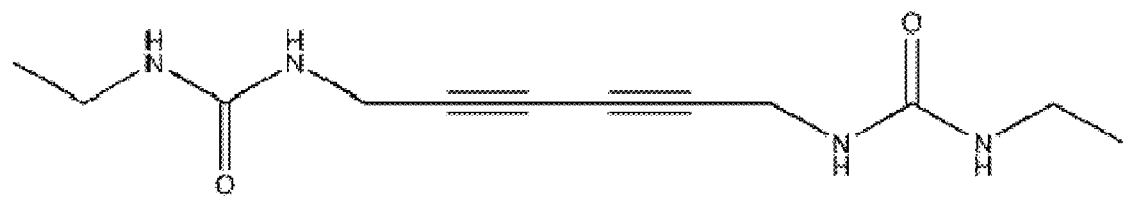
FIG. 2 is a skeletal drawing of a diacetylenic monomer molecule.
Figure 3:
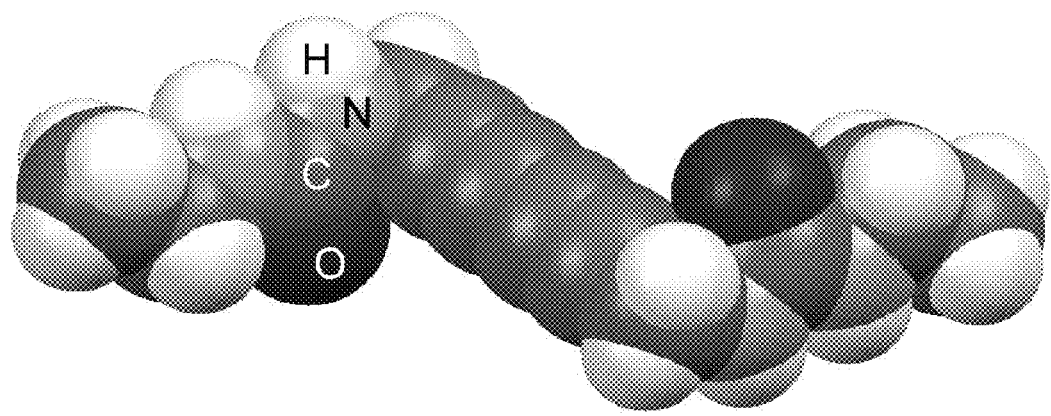
FIG. 3 shows a space-filling model of a diacetylenic monomer molecule.

More detailed models of two diacetylenic compounds are shown in FIGS. 2 and 3. FIG. 2 illustrates the skeletal structure of 2,4-hexadiyn-1,6-bis(ethylurea) monomer molecule and FIG. 3 illustrates space-filling models of 2,4-hexadiyn-1,6-bis(ethylurea), upper model, and 2,4-hexadiyn-1,6-bis(propylurea), lower model.

These models of the mechanism of action of diacetylenic monomer polymerization are believed accurate, but are probably not comprehensive, i.e. other mechanisms may also come into play. Furthermore, they are insufficiently detailed for predictive modeling that could help identify compounds, processing conditions, additives, or other modifications that would provide new diacetylenic monomers with new indicator-related reactivities or reactivity profiles.

For example, it would be desirable to have more crystallographic and other information regarding unit cell dimensions and angles, atomic spacing and conformation in both the diacetylenic monomer and the corresponding polymer.

Useful such information might be provided by X-ray crystallographic data. However, little X-ray crystallographic data is believed available owing to the difficulty of providing crystals of a reactive diacetylenic monomer of sufficient size for comprehensive X-ray crystallographic studies. Accordingly, for these and other purposes, it would be desirable to provide relatively large crystals of a diacetylenic monomer, for example crystals having a dimension of at least about 0.2 mm.

While the invention is not limited by any particular theory, the way in which diacetylenic molecules pack together in crystals is understood to relate to the polymerizability of crystallites used for time-temperature indicators. For these relatively complex molecules, it is believed not presently possible reliably to predict crystal structure from knowledge of the monomer structure alone. Hence, as stated, the discovery of a new crystal phase for a given diacetylene monomer offers the potential to significantly expand the commercial applications opportunities for a given diacetylenic monomer by providing a new set of time-temperature parameters for reaction and correspondingly increased ability to closely match the time-temperature characteristics for the degradation of perishable products or the desired degree of maturation for maturing products.

Some embodiments of the invention comprise methods of altering or modifying the reactivity of a known or newly identified or newly synthesized diacetylenic monomer. The reactivity modification method can be a method of crystallizing, or recrystallizing, the diacetylenic monomer from solution, which method comprises controlling at least one crystallization parameter such as particle size, particle morphology, crystal structure, crystal defects, solvent molecules included in the crystal and thermal history to obtain a diacetylenic monomer having a tuned time-temperature dependence of color response.

While the invention is not limited by any particular theory, it is known that the polymerization reaction providing the color change that makes diacetylenic monomers useful in ambient condition indicators is directed, or influenced, by the diacetylenic monomer's crystal structure. It is contemplated that in crystals of polymerizable diacetylenic monomer, the stacked diacetylenic monomer molecules comprising the crystal are largely arranged in a lattice that can accommodate the transition from monomer to polymer with only small dimensional changes occurring between adjacent aligned monomer molecules in the synthesis of the polymer molecule. It is also contemplated that the necessary small dimensional changes may occur more readily at crystal surfaces and at crystal structural defects where diacetylenic monomer molecules in the lattice have more freedom to move. These considerations are believed helpful to understanding certain aspects of the invention described herein which relate to altering or modifying the reactivity of a diacetylenic monomer by controlling a crystallization parameter, such as one of the crystallization parameters described herein.

In order to crystallize or recrystallize a diacetylenic monomer from solution it is necessary to provide a suitable solvent system for the diacetylenic monomer. As the term is used herein a "solvent system" can comprise one or more solvents. Desirably, the solvent system is one that dissolves the diacetylenic monomer at a useful loading, at an acceptable temperature, and which does not react with the diacetylenic monomer under the recrystallization conditions. When recrystallizing dissolved diacetylenic monomers powders from heated supersaturated solutions of the diacetylenic monomers care is desirable to avoid undesired polymerization which is driven by temperature and time. For this reason, difficulty can occur, in some cases, in attempting to grow large crystals, for example crystals having a dimension greater than 2 mm, of pure diacetylenic monomer, from a supersaturated solution of the diacetylenic monomer, if this requires heating over extended periods of time. Difficulty can also occur, in some cases, in attempting to grow large crystals from a saturated room temperature, or colder, solution owing to limited solubility of the diacetylenic monomer at these temperatures.

Additionally, the cost of processing a diacetylene monomer or mixture of monomers into printed indicator devices can be reduced by the discovery of solvents that are capable of dissolving an adequate concentration of diacetylenic monomer or mixture of monomers. Moreover, diacetylenic monomers are sometimes conveniently precrystallized before formulation as an ink which can be printed, for which purpose the availability of a choice of solvents providing good solubility can be desirable.

Accordingly, it would be useful to identify one or more solvent systems that can ameliorate one or more of these problems.

Solvent Mapping

Generally stated, the invention comprises, in one aspect, a method of preparing a solvent system for dissolving a diacetylenic compound which comprises providing a solvent map plotting the polar solubility parameters of a number of prospective solvents for the diacetylenic compound against the hydrogen bond solubility parameters of the prospective solvents to provide a solubility parameter point for each prospective solvent. In addition the method includes identifying a solubility region for the diacetylenic compound from information regarding the solubility of the diacetylenic compound in at least three liquids, the diacetylenic compound not being insoluble in any one of the liquids. Desirably, the solubility region is a contiguous area of polar and hydrogen bond solubility parameters associated with desired solution properties. The method further includes selecting and employing in the solvent system either a prospective individual solvent having a solubility parameter point lying within the solubility region and not being one of the liquids providing information regarding the solubility of the diacetylenic compound, or a combination of prospective solvents having a combination solubility parameter point lying within the solubility region. The method of preparing a solvent system can, if desired, include mixing the prospective solvent or prospective solvents Pursuant to the invention it has been determined that the solubility of a diacetylenic monomer can be described in terms of thermodynamic properties, for example solubility parameters such as those described by Charles Hansen and known as Hansen's solubility parameters. Hansen described three different solubility parameters which relate to three different types of interaction between the solvent molecules, a dispersive parameter, $\delta_d$, a polar parameter, $\delta_p$, and a hydrogen bonding parameter, $\delta_h$. The solubility parameters are measured in units of the square root of megapascals, $MPa^{1/2}$.

The three solubility parameters can be represented as the co-ordinates for a solubility point on a chart plotted in three dimensions, one for each parameter. According to the Hansen theory, the closer two molecules are to each other in this three dimensional space, the more likely they are to dissolve into each other. Solubility parameters for many solvents can be found in, for example, "*Hansen Solubility Parameters: A user's handbook*", C. M. Hansen, 2000, CRC Press, ISBN 0-8493-1525-5. Also provided is a method for estimation of solubility parameters that are not tabulated in the reference.

While they may be useful in some circumstances, a number of limitations are usually applicable. For example, the parameters are an approximation, bonding between molecules is more subtle than the three parameters might suggest. Molecular shape and size can be relevant as can be other types of bonding such as induced dipole, van der Waals and electrostatic interactions. Accordingly, it can be desirable to experimentally verify solubility predictions derived from the use of Hansen solubility parameters.

Also, the Hansen solubility parameters are generally unknown for diacetylenic monomers. Although Hansen solubility parameters can sometimes be calculated for relatively simple compounds, the two triple bonds present in diacetylenic compounds, and other factors, can introduce uncertainties into the calculations so that reliable figures cannot be calculated for some diacetylenic monomers.

One embodiment of the present invention comprises a method of identifying a new solvent system for a particular diacetylenic monomer which utilizes Hansen solubility parameters but does not require knowledge of the solubility parameters of the intended solute, the diacetylenic monomer. The invention includes solutions of the diacetylenic monomer in the newly identified solvent or solvents.

For example, solubility experiments can be conducted to determine or verify the solubilities of the diacetylenic monomer of interest in a number of known solvents. The results of these solubility experiments can be graphically represented or mapped or otherwise logically identified, on a chart or map of some or all of the Hansen solubility parameters for a group of solvents. The solvent map data can then be used to identify other solvents for the diacetylenic monomer by defining a region on the map of solubility parameter coordinates which can be expected to correspond with enhanced diacetylenic monomer solubility.

The Hansen solubility parameters can be provided for a body of solvents comprising: known solvents for the diacetylenic monomer of interest in which the diacetylenic monomer has a known solubility; nonsolvents in which the diacetylenic monomer is known to have little or no solubility; and prospective solvents in which the solubility of the diacetylenic monomer is unknown.

Any suitable number of known solvents can be employed to provide data regarding the solubility of the diacetylenic monomer and help define a solubility region for the diacetylenic monomer. Some embodiments of the invention employ data from two or three known solvents. Other embodiments employ data from four or five or more known solvents. For example, the information used to identify the solubility region can comprise information about the solubility of the diacetylenic compound in at least five liquids selected from the group consisting of alcohols, acids, water, aromatic compounds, nitrogen-containing compounds, esters, glycols, halogenated organic compounds, alkanes, and mixtures of the foregoing liquids.

The number of known solvents whose solubility data is employed can be from 2 to about 20 or more. Solubility data for a relatively small number of solvents, for example from about 3 to about 10, are employed in some embodiments of the invention.

If desired, solubility data from a larger number of solvents can be employed. Desirably, but not essentially, solvents having parameters in different parts of the chart can be employed. When a region of probable peak solubility has been identified, if desired, additional data from solvents on opposite sides of the region identified, can be employed. For example additional solvents can be selected that have solubility parameters such that a straight line from the solvent's solubility point to the solubility point of another solvent passes through the region of probable peak solubility.

The solvent map can comprise a number of solubility points for each of the known solvents plotted against the solubility parameters. Each solubility point is defined by coordinates of the respective solubility parameters in three-dimensional space. For simplicity, some embodiments of the invention can utilize data for two of the three parameters, for example, the polar parameter and the hydrogen bonding parameter, so that the solubility points can be mapped in two-dimensional space. The solvent map can have two or three axes defining the space in which the solubility points are plotted according to whether two or all three Hansen parameters are employed.

In one embodiment of the invention, known solubility points are plotted against the hydrogen bonding parameter and the polar parameter, with the hydrogen bonding parameter arbitrarily being on the y-axis and the polar parameter can being on the x-axis. In this embodiment of the invention, for simplicity, the dispersion parameter is ignored or considered empirically. If desired, the dispersion parameter can be considered in connection with some, but not all solvents, as will be explained herein.

In another embodiment of the invention, the dispersion parameter is plotted in a third dimension, on a z-axis, or in another suitable manner, and the method is extended into the third dimension, as will be apparent to a person of ordinary skill in the art in light of this disclosure. Other embodiments of the invention employ either polar parameter data or hydrogen parameter data, together with dispersion parameter data, in a two-dimensional solvent map.

In the solvent map, solvents in which the diacetylenic monomer is known to have a desired solubility can be marked, colored, labeled or otherwise graphically or logically identified, in the solvent map, to distinguish the known solvents from known nonsolvents in the solvent map. The solvent map can be specific to the particular diacetylenic monomer. The desired solubility can have any desired value: for example, a solubility in the range of from about 0.1 percent to about 20 percent. Some embodiments of the invention employ desired solubilities of about 0.5, 1, 4, 7, 10 and 13 percent, respectively. Solvents providing at least the desired solubility can be marked while solvents known to provide a lower solubility, or in which the particular monomer is insoluble, are not marked or are marked differently.

Solubilities expressed in percentages herein are to be understood as being by weight of the solute based on the weight of the solution. Solubilities can be heated solubilities or room temperature solubilities, as noted herein or as will be apparent from the context.

Thus known solvents and known nonsolvents exhibiting a desired solubility or lack thereof for a particular diacetylenic monomer can be identified. From this information, a solubility region embracing combinations of solubility parameters providing enhanced solubility for the diacetylenic monomer can be defined or indicated on the solubility map. The defined solubility region can also embrace the solvent map area between the embraced known solvent points. Optionally, the defined solubility region can also embrace an area or areas adjacent to or contiguous with the known solvent points.

The solubility region for the diacetylenic monomer can be identified from information regarding the solubility of the diacetylenic monomer in at least three liquids in which the diacetylenic monomer is not insoluble. Any suitable number of liquids can be employed according to the solubility information available, for example five, ten or twenty or more liquids.

Usefully, the solubility region can be a contiguous area of polar and hydrogen bond solubility parameters associated with desired solution properties. Also, the defined solubility region can embrace combinations of Hansen parameter values that are associated with the desired solubility. Desirably, the defined solubility region includes all or most of the known solvents providing the desired solubility for the particular diacetylenic monomer. Desirably also, the defined solubility region excludes all or most of the nonsolvents being solvents that do not provide that desired solubility.

If desired the defined solubility region can be bounded by a perimeter line. The perimeter line could be an open shape for example a "V" or a "C" but desirably is a closed loop. Depending upon the solubility data appearing in the solvent map, the closed loop perimeter line can have an irregular or a regular or geometric shape, for example, the shape of an ellipse, oval, circle, triangle, rectangle, polygon, quadrilateral or other suitable shape.

Also, if desired, the perimeter line can be positioned and shaped stochastically, with the assistance of mathematical analysis, to define the line according to probabilities that the combinations of Hansen parameters embraced in the defined solubility region will be possessed by solvents having, or not having, the desired solubility properties. Alternatively, the perimeter line can be determined empirically, for example by eye.

If desired, the solubility region can be defined to embrace combinations of solubility parameters that are expected to provide a certain minimum solubility of the diacetylenic monomer, for example, about 1 percent, about 4 percent, about 7 percent or about 10 percent solubility by weight based on the weight of the solution.

Such a solubility region can be helpful in providing diacetylenic solutions comprising a minimum proportion of diacetylenic compound selected from the group consisting of at least about 1, at least about 7 and at least about 10 percent by weight of the diacetylenic compound, based upon the weight of the diacetylenic solution. If desired, the diacetylenic solutions can have still higher concentrations of the dissolved diacetylenic compound or compounds.

In some embodiments of the invention the solubility region is defined or modified according to other factors in addition to solubility parameters. For example a solubility region can be positioned or shaped to avoid solvents or solvent combinations which have too low a boiling point to provide a desired solubility. Also, the solubility region can be positioned or shaped to include or exclude a solvent or solvent system having particular structural features affecting its solvating power for a particular solute that may not be reflected in its Hansen solubility parameters. For example, a solvent having basic character with one or more electron donor groups may have surprising solvating power for a solute having one or more available electron acceptor groups such as the positive end of a dipole whose negative end is less accessible to a potential solvent. However, the invention is not to be limited by any such theory.

Prospective solvents and solvent systems providing, or likely to provide the desired solubility for the diacetylenic monomer can be identified by seeking other solvent systems having solubility points in the defined solubility region.

Surprisingly, it has been found that some useful solvent systems for a diacetylenic monomer can be identified employing a solubility map of hydrogen bonding and polar parameters, without employing the dispersion parameter. The invention includes embodiments wherein the dispersion parameter is ignored.

Some embodiments of the invention comprise solutions of the diacetylenic monomer in a solvent having a solubility parameter point lying in the defined solubility region. Further embodiments of the invention comprise solutions of the diacetylenic monomer in solvent systems having a solubility parameter point in the defined solubility region.

When miscible solvents are combined, their Hansen parameters can be combined by averaging the Hanson parameters for the liquids in the mixture using weighting factors that are the volume fraction of each liquid in the mixture. Thus, on a solvent map the solubility point for a mixture of two solvents will usually be on a straight line between the individual solubility points, at a distance along the line inversely proportional to their respective volume fractions in the mixture. Alternatively, if desired they can be combined by ratio in terms of the respective mass fraction of each solvent in the mixture.

Desirably, the two component solvents of a two-component solvent system can have individual solubility points so positioned on the solvent map that a straight line between them passes through the defined solubility region. The proportion of the solvents in the mixture can be selected or adjusted so that the solubility point of the mixture lies in the defined solubility region.

Some further embodiments of the invention comprise solvent systems having three, four or more components that are miscible with each other and do not react with one another or with the solute. If desired, the solvents can be selected so that the solvent system has a solubility point in a desired solubility region by calculating the parameters of the solubility point to be equal to the average Hansen parameters weighted by the volume fraction of each constituent solvent.

Some exemplary solvent systems include individual solvents as well as mixtures of two or more solvents. Some embodiments of useful solvent system comprise at least one component solvent which is a poor solvent or a nonsolvent for the diacetylenic compound or compounds to be dissolved. The solvents in a mixture to be employed in the practice of the invention desirably can be completely miscible one with the other.

One solvent system useful in the practice of the invention comprises two poor but miscible solvents or nonsolvents for the diacetylenic compound or compounds, for example ethyl alcohol and water. Another useful solvent system comprises one or more relatively good solvents for the diacetylenic monomer or monomers, for example a solvent or solvents capable of dissolving at least 1 percent by weight of the diacetylenic monomer, mixed with one or more poor solvents or nonsolvents for the diacetylenic compound or compounds.

To prepare a solvent map to identify prospective new solvents for a diacetylenic monomer, some information as to the solubility of the diacetylenic monomer in a number of solvents is required, as described herein. If adequate solubility information is not available in the art, solubility tests can be performed.

Prospective solvents and solvent systems can be selected for testing according to available solubility information for the diacetylenic monomer concerned. Solubility points for each of the selected solvents and solvent systems can be mapped on a plot of hydrogen bonding ($\delta H$), on the Y-axis, versus polar parameters ($\delta P$), on the X-axis or as otherwise described or suggested herein.

If the polar and hydrogen bonding solubility parameters of the diacetylenic monomer are known or can be calculated with confidence, a solubility point for the diacetylenic monomer can also be mapped. A trial solubility region can then be mapped in relation to the diacetylenic monomer solubility point and tested experimentally.

In cases where the polar and hydrogen bonding solubility parameters of the diacetylenic monomer are unknown and cannot be calculated with confidence, a solubility region can be determined from the results of experiments, for example as is illustratively described in Example 1 below. Elevated temperatures can be employed for diacetylenic monomers that display limited solubility properties at room temperature. For example, process temperatures in the range of from about 90 to about 95° C. have been employed for recrystallizing a diacetylenic monomer from an acetic acid solution. Generally, temperatures in a range of about 50 to 100° C., or within other suitable limits, can be employed according to the boiling point of the solvents utilized, the stability of the diacetylenic monomer dissolved, the potential for undesired polymerization and other factors.

In this specification, where a solubility is stated without reference to a temperature, the temperature is to be understood as being any temperature reasonably attainable with the solvent in question, at standard atmospheric pressure, i.e. up to a few degrees Celsius above the boiling point of the solvent, for example not more than 5° C. higher.

Some nonlimiting examples of the practice of the invention will now be described.

EXAMPLE 1

Solubility Tests and Definition of a Solubility Region

Figure 4:
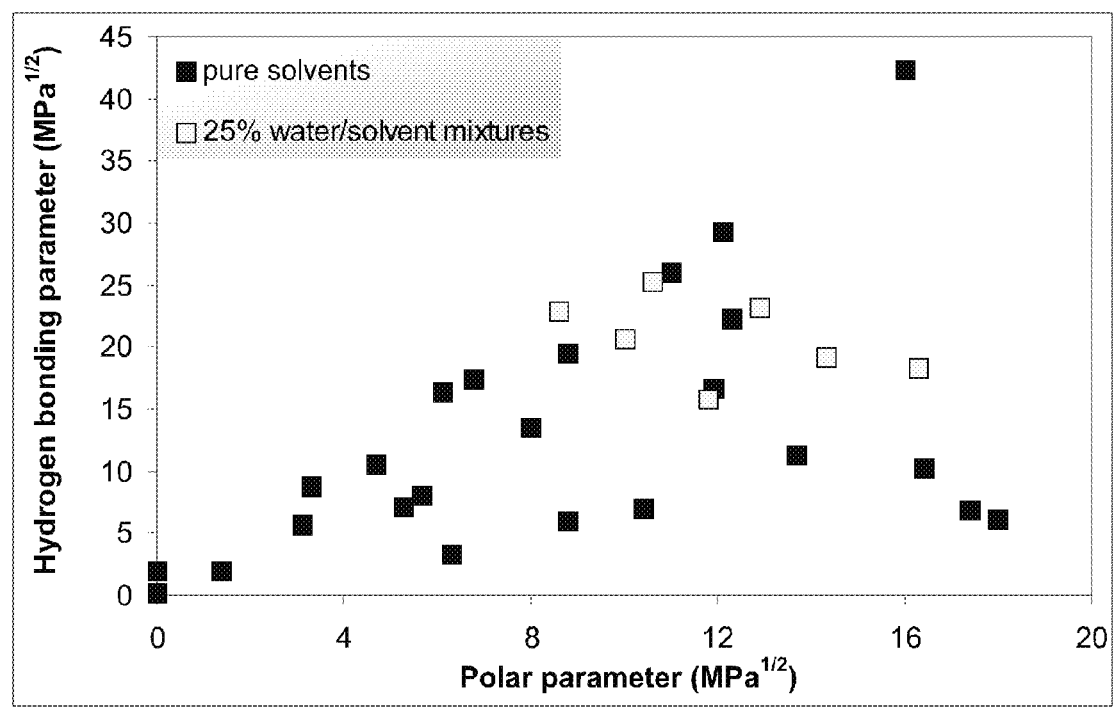
FIG. 4 illustrates a solubility map wherein a number of solubility points of solvents and solvent mixtures are shown.

This example illustrates solvent mapping, testing and solubility region definition for a diacetylenic monomer for which new solvents and solubility information are desired, namely 2,4-hexadiyn-1,6-bis(ethylurea) and for which reliable solubility parameter information is not available. In this example, solubility points are mapped for each of a number of representative samples of a wide range of solvents of different chemical types and physicochemical characteristics, according to their solubility parameters. The solubility points of the representative solvents (filled squares) are mapped on a plot of hydrogen bonding ($\delta H$), on the Y-axis, versus polar parameters ($\delta P$), on the X-axis, generating a map such as that shown in FIG. 4. Also shown in FIG. 4 are solubility points for solvent systems comprising 25 percent by weight water/solvent mixtures (unfilled squares). These mixtures are suggested as potentially useful solvent systems for dissolving 2,4-hexadiyn-1,6-bis(ethylurea) by applying solubility test results for individual solvents (described below) to the FIG. 4 map of their solubility parameters.

Each solvent is tested for its ability to dissolve at least 1 percent by weight 2,4-hexadiyn-1,6-bis(ethylurea) at a temperature not more than 5° C. above the boiling point of the solvent. Because the boiling points of the solvents tested vary widely, ranging from 56° C. to 189° C. the solvents are processed in batches at temperatures of 60, 75, 82, and 90° C., respectively. The process temperature desirably is not greater than 4 to 5° C. above a given solvent's boiling point.

Without solubility information regarding the diacetylenic monomer under consideration, or knowledge of its solubility parameters, it is not feasible to identify in FIG. 4 a region of possible enhanced solubility of the diacetylenic monomer.

Some exemplary solubility data obtainable for 2,4-hexadiyn-1,6-bis(ethylurea) from the above-described solubility test with the solvents indicated, are set forth in Table 1 below along with solubility parameter information for the solvents. Also included in Table 1 are data regarding the 25 percent by weight water/solvent mixtures.

TABLE 1

Solubility Parameters and 1% Solubility Results

| Solvent name | Dispersive parameter | Polar parameter | Hydrogen parameter | Boil T (° C.) | Process T (° C.) | KE soluble at 1% wt? |
|---|---|---|---|---|---|---|
| Acetone | 15.5 | 10.4 | 7.0 | 56 | 60 | No |
| Chloroform | 17.8 | 3.1 | 5.7 | 61 | 60 | No |
| 25% Water/Acetone | 15.5 | 11.8 | 15.8 | 61 | 60 | Yes |
| Methanol | 15.1 | 12.3 | 22.3 | 65 | 60 | Yes |
| THF | 16.8 | 5.7 | 8.0 | 66 | 60 | No |
| n-Hexane | 14.9 | 0.0 | 0.0 | 69 | 75 | No |
| Ethyl acetate | 15.8 | 5.3 | 7.2 | 77 | 75 | No |
| Acrylonitrile | 16.5 | 17.4 | 6.8 | 77 | 75 | No |
| Ethanol | 15.8 | 8.8 | 19.4 | 78 | 75 | Yes |
| Benzene | 18.4 | 0.0 | 2.0 | 80 | 75 | No |
| Cyclohexane | 16.8 | 0.0 | 0.2 | 81 | 82 | No |
| 25% Water/IPA | 15.7 | 8.6 | 22.9 | 81 | 82 | Yes |
| Acetonitrile | 15.3 | 18.0 | 6.1 | 82 | 82 | No |
| 2-Propanol (IPA) | 15.8 | 6.1 | 16.4 | 82 | 82 | Yes |
| 25% Water/Ethanol | 15.7 | 10.6 | 25.2 | 83 | 82 | Yes |
| 1-Propanol | 16.0 | 6.8 | 17.4 | 97 | 82 | Yes |
| Water | 15.5 | 16.0 | 42.4 | 100 | 90 | No |
| 25% Water/formic acid | 14.6 | 12.9 | 23.1 | 100 | 90 | Yes |
| Formic acid | 14.3 | 11.9 | 16.6 | 101 | 90 | Yes |
| Toluene | 18.0 | 1.4 | 2.0 | 111 | 90 | No |
| 25% Water/acetic acid | 14.8 | 10.0 | 20.7 | 113 | 90 | Yes |
| Pyridine | 19.0 | 8.8 | 5.9 | 115 | 90 | Sparingly |
| Acetic acid | 14.5 | 8.0 | 13.5 | 118 | 90 | Yes |
| 25% Water/DMF | 16.9 | 14.3 | 19.1 | 140 | 90 | Yes |
| DMF | 17.4 | 13.7 | 11.3 | 153 | 90 | Yes |
| Cellosolve ® acetate | 16.0 | 4.7 | 10.6 | 156 | 90 | No |
| E3EP | 16.1 | 3.3 | 8.8 | 166 | 90 | No |
| 25% Water/DMSO | 17.7 | 16.3 | 18.3 | 167 | 90 | Yes |
| 1,2-Dichlorobenzene | 19.2 | 6.3 | 3.3 | 179 | 90 | No |
| Glycerol | 17.4 | 12.1 | 29.3 | 182 | 90 | No |
| DMSO | 18.4 | 16.4 | 10.2 | 189 | 90 | Yes |
| Ethylene glycol | 17.0 | 11.0 | 26.0 | 197 | 90 | Yes |

TABLE 1-continued

Solubility Parameters and 1% Solubility Results

| Solvent name | Dispersive parameter | Polar parameter | Hydrogen parameter | Boil T (° C.) | Process T (° C.) | KE soluble at 1% wt? |
|---|---|---|---|---|---|---|
| Average | 16.4 | 9.1 | 13.9 | | | |
| +/− Std. deviation | 1.3 | 5.2 | 9.5 | | | |

As used in Table 1, and elsewhere herein, "DMF" indicates dimethyl formamide, "DMSO" indicates dimethyl sulfoxide, "E3EP" indicates ethyl 3-ethoxypropionate" and "THF" indicates tetrahydrofuran.

The results for the individual solvents in Table 1 indicate five that dissolve at least 1 percent by weight of 2,4-hexadiyn-1,6-bis(ethylurea) and could accordingly warrant further study. These solvents are dimethyl sulfoxide (DMSO), acetic acid, N,N-dimethyl formamide (DMF), ethanol (EtOH), and ethylene glycol. As expected, following use of the solubility map, the water/solvent mixtures all dissolve at least 1 percent by weight of 2,4-hexadiyn-1,6-bis(ethylurea).

Applying the Table 1 results from the 1 percent weight solubility test on the map of Hansen solubility parameters enables a distinct region on the map to be defined, in terms of polar and hydrogen bonding parameters where 2,4-hexadiyn-1,6-bis(ethylurea) is soluble at reasonable processing temperatures. This can be done without having information regarding a solubility point and values for the solubility parameters of the solute, 2,4-hexadiyn-1,6-bis(ethylurea).

EXAMPLE 2

Further Solubility Tests

The Example 1 solubility tests are then repeated for different solute concentrations, in this case 4 percent, 7 percent, and 10 percent by weight of 2,4-hexadiyn-1,6-bis(ethylurea) in each of the solvents demonstrating at least 1 percent solubility in the previous test as well as the water/solvent mixtures. A 90° C. water bath is employed to maintain the solvent or solution temperature and results obtainable are tabulated in Table 2 below, solubility parameter information again being included to facilitate understanding of the data for acetone and water, for reference.

TABLE 2

Solubility Trial Results at Various Solubilities

| Solvent name | Polar parameter ($MPa^{1/2}$) | Hydrogen parameter ($MPa^{1/2}$) | Boil Temp (° C.) | Is KE soluble at | | | |
|---|---|---|---|---|---|---|---|
| | | | | 1%? | 4%? | 7%? | 10%? |
| Acetone | 10.4 | 7.0 | 56 | No | No | No | No |
| 25% Water/Acetone | 11.8 | 15.8 | 61 | Yes | Yes | No | No |
| Methanol | 12.3 | 22.3 | 65 | Yes | Yes | No | No |
| Ethanol | 8.8 | 19.4 | 78 | Yes | No | No | No |
| 25% Water/IPA | 8.6 | 22.9 | 81 | Yes | No | No | No |
| 2-Propanol (IPA) | 6.1 | 16.4 | 82 | Yes | No | No | No |
| 25% Water/Ethanol | 10.6 | 25.2 | 83 | Yes | Yes | No | No |
| 1-Propanol | 6.8 | 17.4 | 97 | Yes | No | No | No |
| Water | 16.0 | 42.4 | 100 | No | No | No | No |
| 25% water/formic acid | 12.9 | 23.1 | 100 | Yes | Yes | Yes | No |
| Formic acid | 11.9 | 16.6 | 101 | Yes | Yes | Yes | Yes |
| 25% water/acetic acid | 10.0 | 20.7 | 113 | Yes | Yes | Yes | No |
| Pyridine | 8.8 | 5.9 | 115 | Yes | No | No | No |
| Acetic acid | 8.0 | 13.5 | 118 | Yes | Yes | Yes | Yes |
| 25% Water/DMF | 14.3 | 19.1 | 140 | Yes | Yes | Yes | No |
| DMF | 13.7 | 11.3 | 153 | Yes | Yes | Yes | Yes |
| 25% Water/DMSO | 16.3 | 18.3 | 167 | Yes | Yes | No | No |
| DMSO | 16.4 | 10.2 | 189 | Yes | Yes | Yes | Yes |
| Ethylene Glycol | 11.0 | 26.0 | 197 | Yes | No | No | No |

These results demonstrate the practice of various aspects of the invention. For example, two new solvents for 2,4-hexadiyn-1,6-bis(ethylurea) providing solubilities in excess of 10 percent are identified, namely formic acid and dimethyl sulfoxide. Formic acid can solvate nearly 13% 2,4-hexadiyn-1, 6-bis(ethylurea) by weight at room temperature.

Also, it can be noted that two non-solvents for 2,4-hexadiyn-1,6-bis(ethylurea), namely water and acetone, can be combined together, combining their solubility parameters, to provide a solvent system in which 2,4-hexadiyn-1,6-bis(ethylurea) has an unexpectedly good solubility of at least 4 percent by weight.

Furthermore, surprisingly, a 25% water/ethanol mixture (1 part by weight water combined with 3 pars by weight ethanol) provides a better 2,4-hexadiyn-1,6-bis(ethylurea) solubility, at least 4 percent by weight, than does pure ethanol for which the 2,4-hexadiyn-1,6-bis(ethylurea) solubility is less than 4 percent by weight, notwithstanding the fact that 2,4-hexadiyn-1,6-bis(ethylurea) is insoluble in water.

Careful consideration of such findings suggests one or more regions of enhanced or optimal 2,4-hexadiyn-1,6-bis(ethylurea) solubility lying within a narrow range of solubility parameters. Diacetylenic monomer solution embodiments and other embodiments of the invention can employ one or more combinations of solvents that are completely miscible and have solubility parameters that can be combined to lie in such an enhanced or optimal solubility region for the particular diacetylenic monomer.

Figure 5:
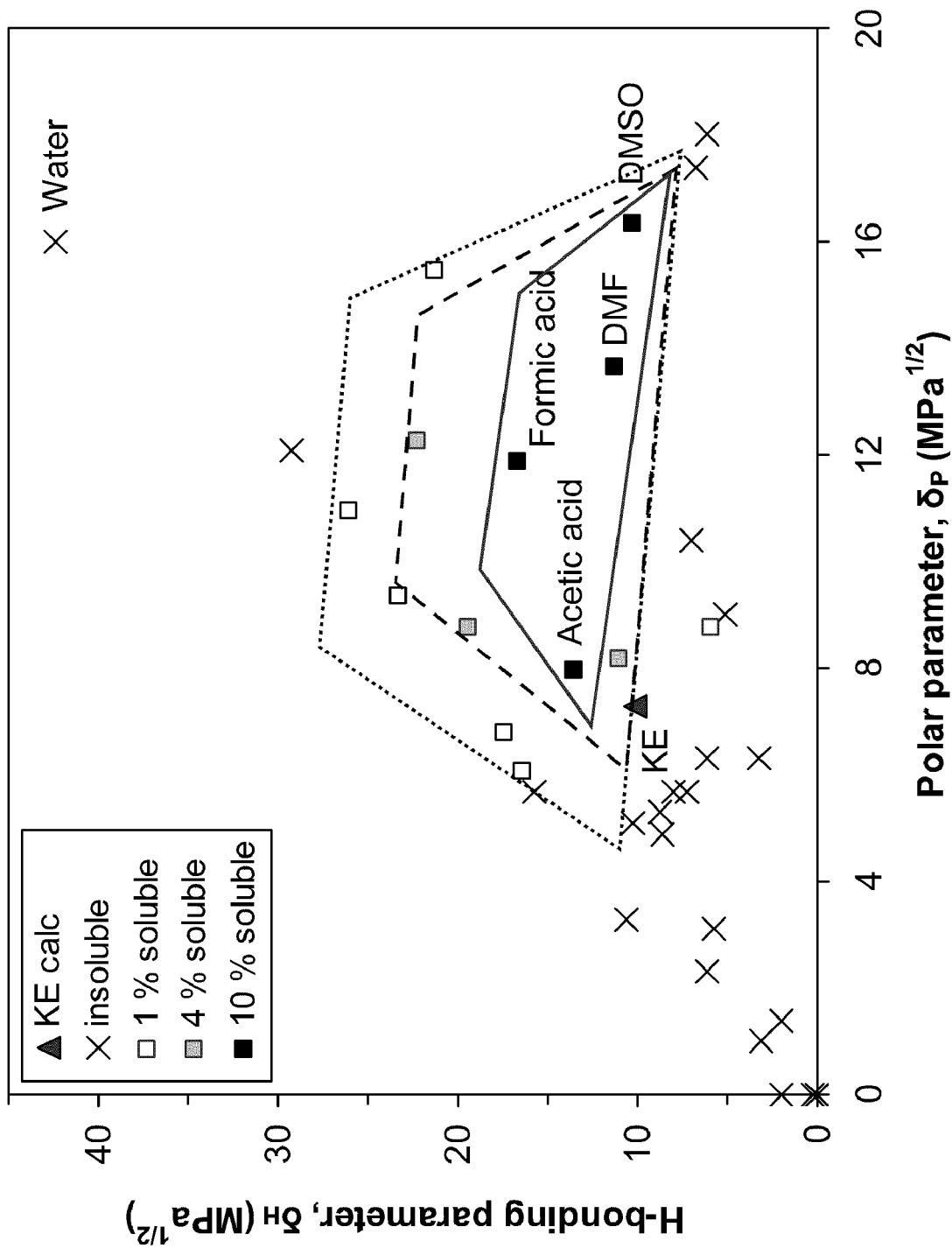
FIG. 5 illustrates a further solubility map wherein a number of solubility regions are defined according to the invention.

Several ways of applying some of the 2,4-hexadiyn-1,6-bis (ethylurea) solubility results shown in Table 2 to a solubility map such as is shown in FIG. 4, are illustrated in FIG. 5.

Referring to FIG. 5, the parameter quantifying a solvent's dipole strength, the polar parameter, sometimes referenced "$\delta P$", is plotted along the X-axis and the parameter quantifying the solvent's hydrogen-bonding strength, the hydrogen bonding parameter, sometimes referenced "$\delta H$", is plotted along the Y-axis. The units in each case are megapascals$^{1/2}$, MPa$^{1/2}$. In this embodiment of the invention, the dispersion parameter, sometimes referenced "$\delta P$", is not employed.

In FIG. 5, dark squares indicate solvents providing at least 10 percent solubility, intermediate shaded squares indicate solvents providing at least 4 percent solubility and light squares indicate solvents providing at least 1 percent solubility. "X" indicates a solvent in which 2,4-hexadiyn-1,6-bis (ethylurea) is insoluble or has less than 1 percent solubility. For clarity, most of the solvent names were omitted except for water, acetone and solvents able to dissolve 10% weight 2,4-hexadiyn-1,6-bis(ethylurea).

Three solubility regions having the approximate solubility parameters that are apparently required for threshold solubilities of 1 percent, 4 percent, and 10 percent respectively are shown in FIG. 5. The solubility regions are overlaid one on the other with the largest solubility region embracing solvent systems providing at least 1 percent 2,4-hexadiyn-1,6-bis (ethylurea) solubility. A smaller region within this large region provides at least 4 percent 2,4-hexadiyn-1,6-bis(ethylurea) solubility and the smallest region, which lies wholly within this smaller region, provides at least 4 percent 2,4-hexadiyn-1,6-bis(ethylurea) solubility. As defined in FIG. 5, each solubility region has a trapezoidal shape. However, the solubility regions can have other shapes.

While the invention is not to be limited by any particular theory, it is contemplated that the low boiling point of acetone may not allow the solution to become hot enough to attain the solubilities for 2,4-hexadiyn-1,6-bis(ethylurea) displayed by the other four solvents in the smallest solubility region, all of which have boiling points of over 100° C.

With the assistance of a solubility map such as that shown in FIG. 5, various practical guidelines for identifying useful solvents can be determined, according to solubility needs. For example, to dissolve at least about 1 percent by weight of 2,4-hexadiyn-1,6-bis(ethylurea), a solvent system having a polar solubility parameter in the range of from about 7.5 to about 16.6 MPa$^{1/2}$ and a hydrogen bonding parameter in the range of from about 8.5 to about 26.0 MPa$^{1/2}$ can be employed. To dissolve at least about 4 percent by weight of 2,4-hexadiyn-1,6-bis(ethylurea), a solvent system having a polar solubility parameter in the range of from about 7.7 to about 16.5 MPa$^{1/2}$ and a hydrogen bonding parameter in the range of from about 9.0 to about 22.5 MPa$^{1/2}$ can be employed. To dissolve at least about 10 percent by weight of 2,4-hexadiyn-1,6-bis(ethylurea), a solvent system having a polar solubility parameter in the range of from about 8.0 to about 16.4 MPa$^{1/2}$ and a hydrogen bonding parameter in the range of from about 10.0 to about 17.0 MPa$^{1/2}$ can be employed.

Thus, data such as is shown in Table 2 can be used to identify regions of desirable solubility on a solubility map of the solvent solubility parameters. The solubility map can, in turn, be used to identify one or more new solvent systems for the diacetylenic monomer of interest.

Figure 6:
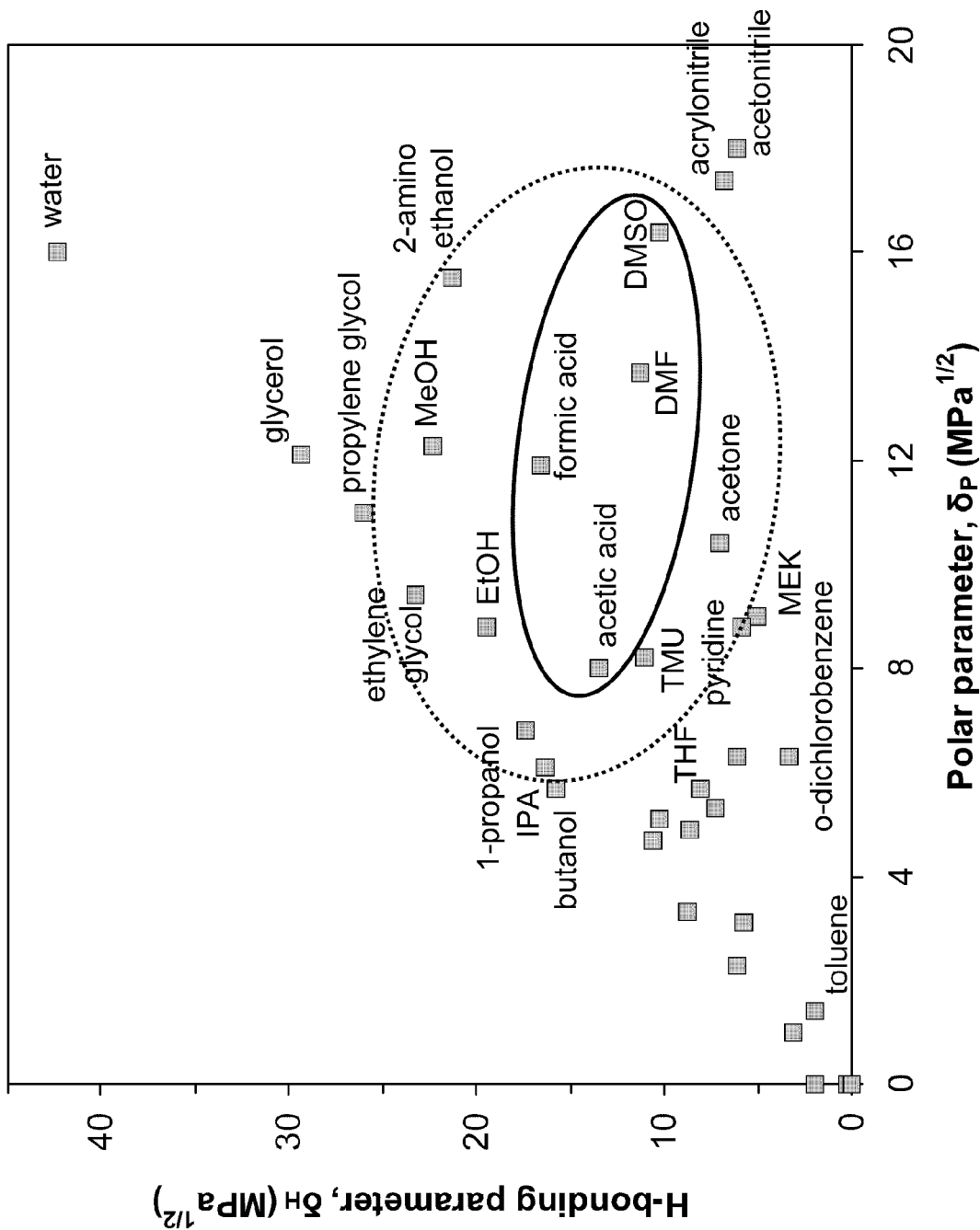
FIG. 6 illustrates another solubility map wherein additional solubility regions are defined according to the invention.

The example of a two-dimensional solvent map depicted in FIG. 6 shows the solubility points for a number of solvents and a number of defined solubility regions illustrative of what can be empirically determined from solubility tests on the solubility of a diacetylenic monomer such as 2,4-hexadiyn-1,6-bis(ethylurea) in selected solvents systems.

FIG. 6 is generally similar to FIG. 5, with the difference that in FIG. 6 instead of the trapezoidal solubility regions defined in FIG. 5, two elliptical solubility regions of different sizes are defined, the smaller lying wholly within the larger and embracing solubility points that are expected to provide higher solubilities for 2,4-hexadiyn-1,6-bis(ethylurea). The larger ellipse is defined to embrace a range of solubility parameters expected to be appropriate for solvents and solvent systems providing a minimum desired 2,4-hexadiyn-1, 6-bis(ethylurea) solubility. The smaller ellipse is defined to embrace a range of solubility parameters expected to be appropriate for solvents and solvent systems providing a higher or optimal desired 2,4-hexadiyn-1,6-bis(ethylurea) solubility. Also, the various solubility points are labeled with the solvent names.

Figure 7:
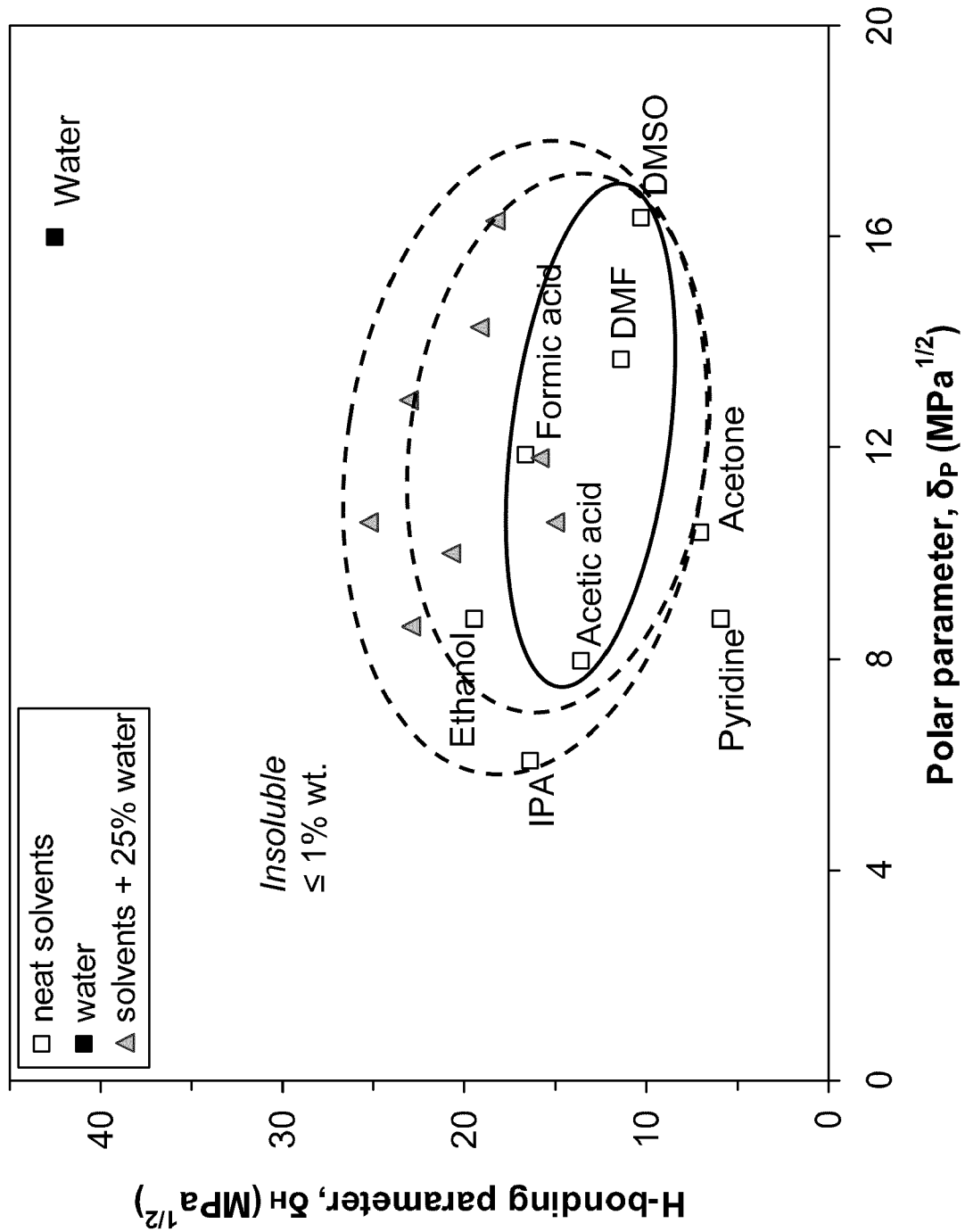
FIG. 7 illustrates an additional solubility map wherein still further solubility regions are defined according to the invention.

The solubility region perimeter lines in FIGS. 5-7 can be determined by interpolation from the known solubilities and from the new solubilities identified in solubility tests such as described in Examples 1 and 2, or in other suitable manner.

FIG. 7 is generally similar to FIG. 6 with the difference that solubility points for the water/solvent mixtures shown in Table 2 are included and identified, while individual solvent solubility points, other than water, are not identified.

Referring to FIG. 7, it can be seen that water lies well outside the enhanced solubility regions shown consistently with its being, as stated above, a non-solvent for the particular diacetylenic monomer tested, namely 2,4-hexadiyn-1,6-bis (ethylurea). Surprisingly, water can be mixed with other solvents with which it is miscible to provide new solvent systems having good solubility for 2,4-hexadiyn-1,6-bis(ethylurea). Some of these mixtures are marked with triangles in FIG. 7. For example, 2,4-hexadiyn-1,6-bis(ethylurea) has only limited solubility in acetone alone but has a useful solubility in an acetone-water mixture. A straight line between the solubility points for acetone and water passes through the region of peak solubility for 2,4-hexadiyn-1,6-bis(ethylurea). A mixture having a minor proportion of water, 25% in the test example herein, locates the mixture solubility point in the peak solubility region.

Figure 8:
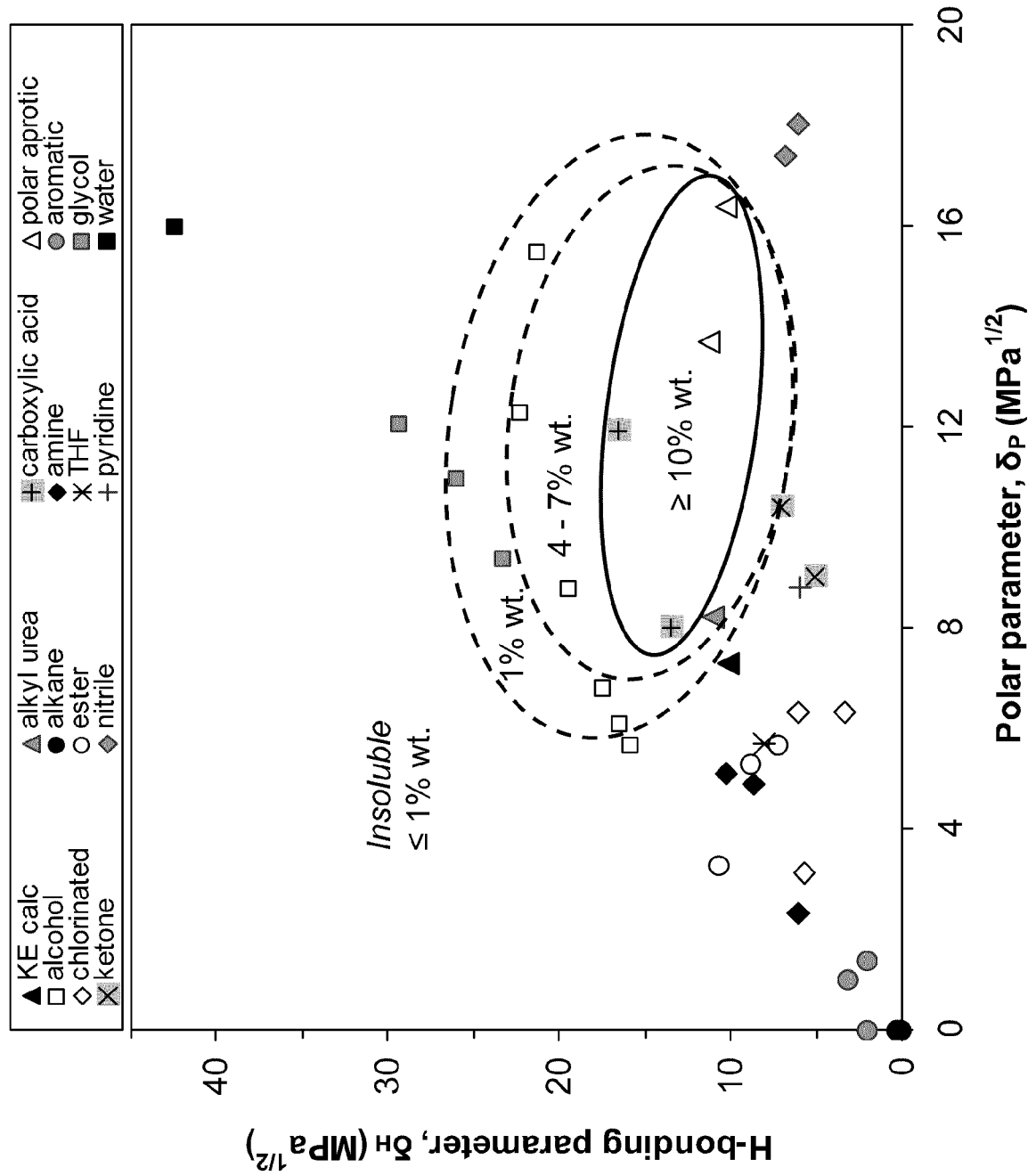
FIG. 8 illustrates another solubility map wherein further solubility regions according to the invention are defined and a calculated solubility point for a diacetylenic monomer is shown.

The solubility map shown in FIG. 8 comprises solubility points for a number of solvents listed by functional group, and for the individual solvents water and tetrahydrofuran. The solubilities are determined in trials at temperatures up to 90° C. or near the boiling point of a given solvent, as described in Example 1.

Using the data obtained, elliptical solubility regions are defined for solubility coordinates correlated with solubilities of at least about 1% by weight, of at least about 4% by weight and of at least about 10% by weight of 2,4-hexadiyn-1,6-bis (ethylurea).

Also shown in FIG. 8 is an example of a calculated solubility point for a diacetylenic monomer, in this case 2,4-hexadiyn-1,6-bis(ethylurea), which is referenced "KE" in FIG. 8 and some other figures of the accompanying drawings. The calculated solubility point, indicated by a dark triangle in FIG. 8 is determined by calculation of its Hansen solubility parameters according to the method of van Krevelyn, with a listing of group increments. The calculated values, in MPa$^{1/2}$, are: $\delta D=20.8$, $\delta P=7.3$, and $\delta H=10.1$. These calculated values appear to be reasonable, but do not agree well with experiment: 2,4-hexadiyn-1,6-bis(ethylurea) ("KE") falls outside of its own region of solubility. One method of calculating Hansen solubility parameters according to the method of van Krevelyn is described by Brandrup, J.; Immergut, E. H.; Grul E. A., Eds. in Polymer Handbook, 4th ed.; John Wiley & Sons, Inc.: Hoboken, N.J.; 1999; Vol. 2.

Figure 9:
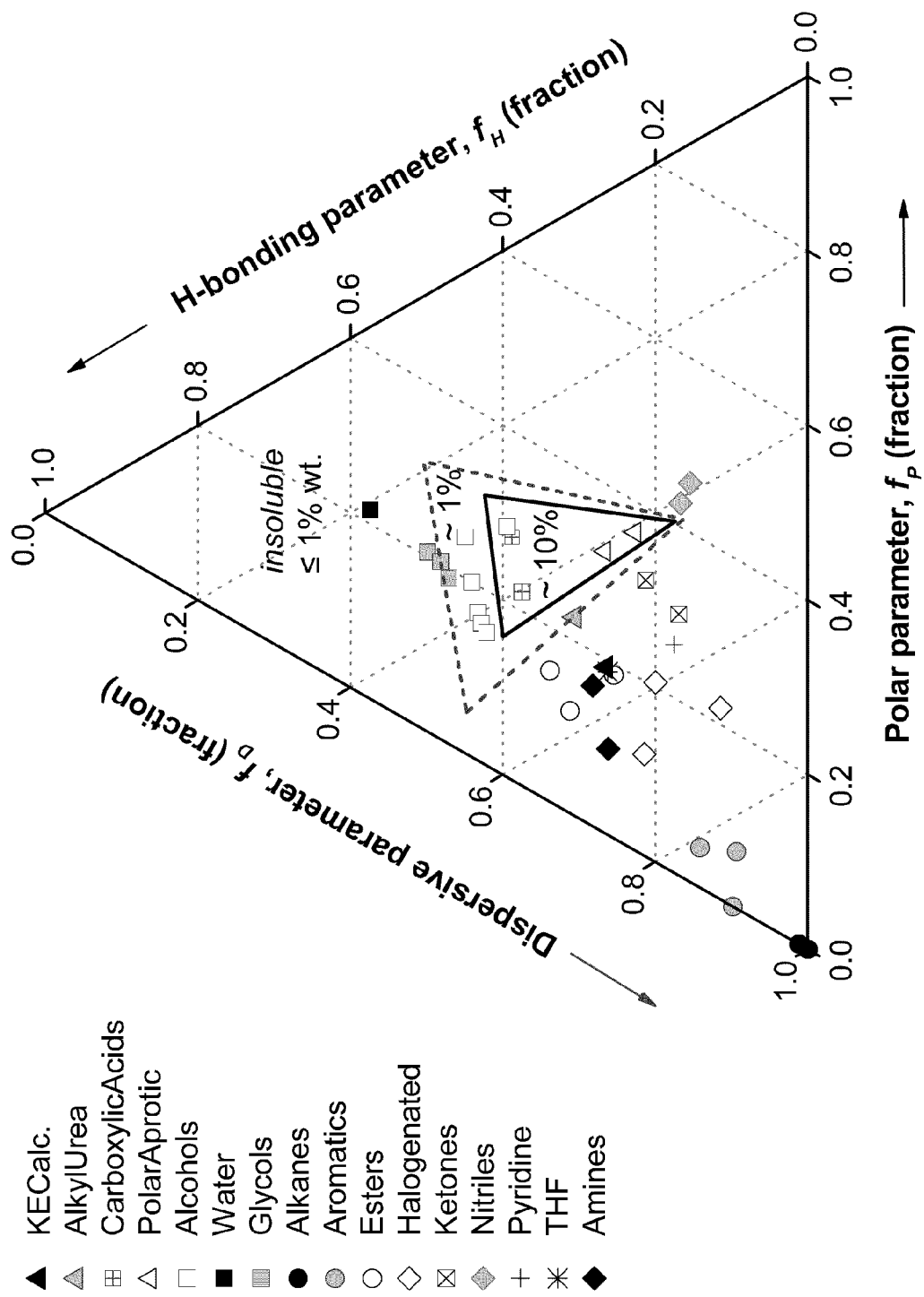
FIG. 9 illustrates an embodiment of three-dimensional solubility map useful in the practice of the invention, in this case a Teas graph.

The solubility map shown in FIG. 9 is an embodiment of what is known as a Teas graph and it plots a third solubility parameter, the dispersion parameter, in addition to the polar and hydrogen bonding parameters plotted in FIGS. 5-8.

In order to plot all three solubility parameters on a single planar graph, an assumption is made that all materials have the same Hildebrand solubility parameter. This is an approximation for convenience. A Hildebrand value is the root mean square average of the three Hansen parameters which are often considered as additive components of the Hildebrand value. Teas graph plots the relative contribution of each of the three component Hansen solubility parameters, (i.e. the dispersion parameter, polar parameter, and hydrogen bonding parameter) to the total Hildebrand value. Solubility parameters can then be expressed in proportions of a whole rather than unrelated parameters. A Teas graph is further described by John Burke in "*Solubility Parameters: Theory and Application*" The Book and Paper Group Annual, Vol. 3, 1984 The American Institute for Conservation of Historic and Artistic Works (AIC).

Approximate solubility points for a variety of groups of solvents are shown in FIG. 9, namely, for carboxylic acids, polar aprotic solvents, glycols, alcohols, alkanes, aromatics, esters, halogenated solvents, ketones, nitrites, as well as for water, pyridine and tetrahydrofuran.

The solubility points for groups are approximate averages for the group and possible variation of the solubility parameters with temperature is ignored, as is the case with the other solubility maps shown.

Two solubility regions indicating zones of enhanced solubility for 2,4-hexadiyn-1,6-bis(ethylurea) are shown, a broken line triangle, intended to correlate approximately with at least about 1% by weight solubility and within that, a solid line triangle intended to correlate approximately with at least about 10% be weight solubility. These regions can fit reasonably well with experimental results. One outlier is pyridine which solvates about 1% by weight 2,4-hexadiyn-1,6-bis(ethylurea), but lies outside the plotted triangles.

Similar results are believed obtainable for 2,4-hexadiyn-1,6-bis(propylurea) (also referenced herein as "KPr") with a three-dimensional solubility map such as that shown in FIG. 9. Other ways of plotting three or more dimensions of solubility parameters will be or become apparent to those skilled in the art.

For some purposes it would be useful to have a solvent which effectively solvates a diacetylenic monomer at room-temperature. Crystal growth can be facilitated at lower temperatures, where polymerization is likely to be less of a factor than at higher temperatures. Also, good room temperature solubility has potential value in downstream processing and manufacturing applications of diacetylenic monomers. Accordingly, some embodiments of the invention include solutions of diacetylenic monomers in solvent systems capable of providing significant room-temperature solubility for a diacetylenic monomer.

For this or other purposes, room temperature solubilities of a diacetylenic monomer, 2,4-hexadiyn-1,6-bis(ethylurea) recrystallized from acetic acid, in a variety of solvent systems can be determined, for example as shown in Table 3, below. Table 3 shows solubilities at a room temperature of 20° C. in weight percent based on the weight of the solution.

TABLE 3

Solubilities of 2,4-hexadiyn-1,6-bis(ethylurea) at 20° C.

| Solvent System | Solubility (wt. % of the Solution) |
|---|---|
| Methyl alcohol "MeOH" | 0.27 |
| Ethyl alcohol | 0.17 |
| Isopropyl alcohol | 0.09 |
| Tetramethyl urea | 0.90 |
| Formic acid | 23 |
| Acetic acid | 0.6 |
| Dichloroacetic acid | 33 |
| Trifluoroaceticacetic acid | 30 |
| DMF | 4 |
| DMSO | 4 |
| Acetone/water 4:1 | 0.16 |
| Ethanol/water 4:1 | 0.18 |

1,1,3,3 tetramethyl urea, also called "tetramethyl urea" and sometimes referenced "TMU" can dissolve up to 7% weight 2,4-hexadiyn-1,6-bis(ethylurea) at a temperature of 90° C. in a closed vial.

Using information regarding solubilities of 2,4-hexadiyn-1,6-bis(ethylurea), such as is shown in Table 3 below, room temperature solutions can be made up for recrystallization, for use as inks to prepare environmental condition indicators or for other purposes. Other diacetylenic monomers solutions can be similarly prepared.

Figure 10:
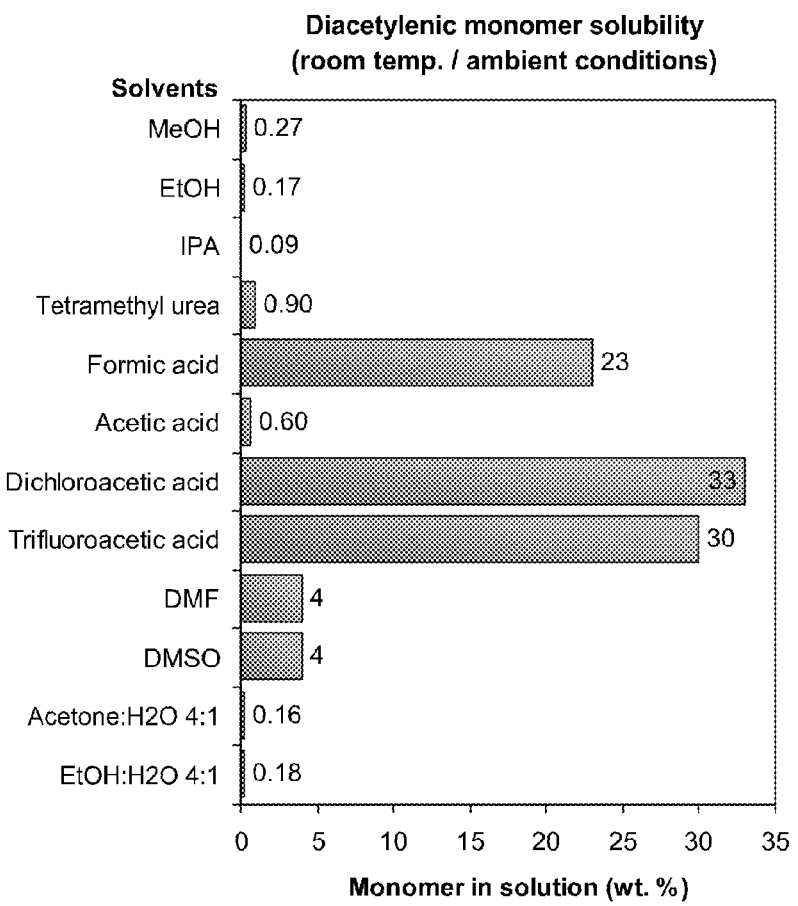
FIG. 10 is a bar chart showing the solubilities of a diacetylenic monomer in various solvent systems at room temperature.

The bar chart shown in FIG. 10 depicts the room-temperature solubilities listed in Table 3 graphically.

As is the case elsewhere herein, the acetone/water and ethanol/water solvent mixtures are given in weight-for-weight proportions in Table 3 and FIG. 10. It can be seen from Table 3 and FIG. 10 that some of the solvent systems displaying elevated solubility at higher temperatures, for example acetic acid and the several aqueous mixtures, have only limited solubility at room temperature.

In contrast, the halogenated solvents and formic acid display excellent room temperature solubility. However, these solvents have well-known handling characteristics that may make them unsuitable for some purposes. A useful aspect of the invention provides new solvent systems for one or more diacetylenic compounds which are environmentally friendly or compatible. An example of an environmentally compatible solvent system is an aqueous solvent system comprising a high proportion of water, for example more than 50 percent by weight water.

The solubilities of other diacetylenic monomers in the solvent systems provided by the invention or employed in the practice of the invention, can be determined by extrapolation or routine experimentation. For example, the solubility of 5,7-dodecadiyn-1,12-bis-n-octadecyl urethane (also "4DOD" herein) in various solvent systems can be determined as described in Example 2A below. 5,7-dodecadiyn-1,12-bis-n-octadecyl urethane ("4DOD") has the following chemical structure

and is radiation sensitive, exhibiting a color change, but relatively insensitive to normal ambient thermal conditions. 5,7-dodecadiyn-1,12 diol bis(n-butoxycarbonyl urethane is another compound having which is radiation sensitive, but relatively insensitive to normal ambient-thermal conditions. The invention includes radiation monitoring devices employing one or more such compounds to provide a visual indication of cumulative exposure to high energy ambient radiation, for example, ultraviolet light, alpha rays, beta rays or other subatomic particle streams, X-rays, gamma rays and/or the like.

EXAMPLE 2A

Solubility of 5,7-dodecadiyn-1,12-bis-n-octadecyl Urethane ("4DOD")

To serve as indicator agent, a thermally insensitive polymerizable diacetylenic monomer, namely 5,7-dodecadiyn-1, 12 diol bis(n-octadecyl urethane), "4DOD" hereinafter, is synthesized in sufficient quantity for preparation of a master batch of ink, by the method described in Yee U.S. Pat. No. 4,215,208 at column 17, lines 47-65 and is stored in a freezer. A small quantity of 4DOD is taken from frozen storage and is tested at room temperature for solubility in various solvent systems employing the following procedure.

100 g of deionized water is weighed into a 200 mL glass beaker. 4DOD powder is added to the glass beaker until the solution is saturated allowing excess 4DOD to remain present as undissolved solid. 75 g of deionized water is weighed into another 200 mL glass beaker, and 25 g acetone is added. 4DOD is then added to the water-acetone solvent system in the glass beaker until the solution is saturated and an excess of 4DOD remains as undissolved solid. 75 g of deionized water is weighed into a third 200 mL glass beaker. 25 g ethanol is added to the water and then 4DOD is added to the water-ethanol mixture until the solution is saturated and an excess of 4DOD remains as undissolved solid. Each solution is stirred on a magnetic plate for 16 hours at a controlled room temperature of about 25° C.

After 16 hours of stirring, 7 g of each solution (soluble portion only, avoiding any undissolved solid material) is transferred to a separate aluminum foil pan. The aluminum foil pans are left to stand under a fume hood for 2 hours to allow any volatile solvent to evaporate, and are then dried in a vacuum oven for one 1 hour. Each aluminum foil pan is then weighed and the solubility of the 4DOD in each solvent system is calculated in terms of the percent of solute based on the weight of the solvent system. Some results obtainable are shown in Table 2A below:

TABLE 2A

Solubility Results for 4DOD

| Solvents | Weight of solution before drying | Weight of Solute after drying | Calculated solubility of 4DOD (wt %) |
|---|---|---|---|
| Water | 7.0 g | 0.00201 g | 0.03% |
| 75% Water 25% Acetone | 7.0 g | 0.70618 g | 10% |
| 75% Water 25% Ethanol | 7.0 g | 0.62184 g | 9% |
| 100% Ethanol | 7.0 g | 2.58206 | 37% |
| 100% Acetone | 7.0 g | 2.21616 | 32% |

As can be seen from the results in Table 2A, under the test conditions, 4DOD has minimal solubility in water. However, environmentally acceptable solvent systems comprising a high proportion of water mixed with ethanol or acetone show a dramatically increased solubility of 4DOD of about 9 or 10 percent by weight of the solvent system. The results also show a remarkably high solubility for 4DOD in the individual organic solvent alone, ethanol or acetone.

The methods of the invention provide flexibility in designing solvent systems for a diacetylenic monomer, for example for 2,4-hexadiyn-1,6-bis(ethylurea). Thus, the solvent maps shown in FIGS. 5-7 are illustrative of solvent maps that can be employed to identify new solvents for a diacetylenic monomer or to create new solvent systems for the diacetylenic monomer, or both. The new solvents and solvent systems can provide new solubility information regarding the diacetylenic monomer useful in the subsequent processing or utilization of the diacetylenic monomer. The new solubility information can comprise new knowledge regarding a solvent system in which the diacetylenic monomer has useful solubility or new quantitative information regarding its solubility in a solvent system.

The following are some examples of individual solvents useful in practicing the invention: methanol, formic acid, dimethyl sulfoxide, ethylene glycol, allyl alcohol, 2-aminoethanol; 1,1,3,3-tetramethylurea; dichloroacetic acid and trifluoroacetic acid.

Some useful solvent systems comprise mixtures of water with another solvent having suitably complementary solubility parameters. The mixture with water can comprise from about 1 to about 40 percent by weight water, based on the weight of the solvent system, from about 4 to about 25 percent by weight water or another suitable proportion. If desired, the other solvent or solvents can have a hydrogen bonding parameter of not more than about 15 $MPa^{1/2}$ and can have a polar bonding parameter of not more than about 18 $MPa^{1/2}$. Some other useful solvent systems comprise nonaqueous mixtures of solvents, including mixtures of non-alcoholic ones of the individual solvents mentioned above with a suitable alcoholic solvent or solvents.

The following are some examples of solvent system mixture embodiments of the invention wherein, in each case, the proportion of water is based upon the weight of the solvent system:

a mixture of acetic acid and water in a proportion of from about 5 percent to about 25 percent of water, the balance being acetic acid;

a mixture of acetone and water in a proportion of from about 5 percent to about 25 percent of water, the balance being acetone;

a mixture of dimethyl formamide ("DMF" herein) and water in a proportion of from about 5 percent to about 25 percent of water, the balance being dimethyl formamide;

a mixture of dimethyl sulfoxide and water in a proportion of from about 0 percent to about 25 percent of water, optionally at least about 5 percent water, the balance being dimethyl sulfoxide;

a mixture of ethanol and water in a proportion of from about 0 percent to about 25 percent of water, optionally at least about 4 percent water, the balance being ethanol;

a mixture of pyridine and water in a proportion of from about 1 percent to about 25 percent of water, optionally at least about 5 percent water, the balance being pyridine;

a mixture of 1,1,3,3-tetramethylurea and water in a proportion of from about 1 percent to about 25 percent of water, optionally at least about 5 percent water, the balance being acetic acid; and a mixture of dimethyl sulfoxide and ethanol in a proportion of from about 10 percent to about 90 percent of water, optionally at least about 30 percent water, the balance being dimethyl sulfoxide, for example an approximately 50:50 mixture.

Accordingly, a solvent system for use in diacetylenic solution embodiments of the invention can be selected from the group consisting of methanol, formic acid, dimethyl sulfoxide, ethylene glycol, aminoethanol; 1,1,3,3-tetramethylurea; allyl alcohol, dichloroacetic acid, trifluoroacetic acid and a mixture of water with one or more of the foregoing solvents wherein the proportion of water based upon the weight of the solvent system is in the range of from about 1 to about 50 percent.

Acetone and water and ethanol and water are further examples of aqueous mixtures that can be employed, with a similar proportion of water. Non aqueous solvent mixtures can also be employed as solvent systems in the practice of the invention.

One embodiment of solvent system useful in the practice of the invention comprises an azeotropic ethanol-water mixture comprising about 95-96 percent by weight ethanol and about 4-5 percent by weight water. The invention includes a saturated solution of a diacetylenic monomer in this azeotropic mixture.

If desired, other miscible solvents can be added to the foregoing mixtures to form ternary, quaternary or more complex solvent systems, as will be apparent from, or suggested by, this disclosure. For example, ternary mixtures of water with two other solvents, for example isopropyl alcohol and dimethyl sulfoxide can be employed. Suitable proportions for such a ternary solvent system include a proportion of up to about 25 percent by weight water the balance being the two other solvents in relative weight proportions of from about 1:2 to 2:1.

Some other useful solvent systems comprise mixtures of miscible solvents wherein the polar solubility parameter and hydrogen bonding solubility parameter of the solvent system each comprise an average of the respective parameters for the individual miscible solvents using as weighting factors the volume fraction of each solvent in the solvent system.

Still further suitable solvent systems will be or become apparent to those skilled in the art in light of this disclosure. For example the polar and hydrogen-bond solubility parameters of a first prospective solvent can be plotted on a solubility map such as that shown in any one of FIGS. 5-9. If the solvent lies within a desired solubility region or envelope for a particular diacetylenic monomer, it can be expected that the prospective solvent can be used alone. If the solubility point for the first prospective solvent lies outside a desired solubility region for the diacetylenic monomer, a solubility map can be utilized, pursuant to the invention, to select a second prospective solvent which can be combined with the first prospective solvent into a solvent system providing a desired solubility for the diacetylenic monomer.

It will be understood that multi-component solvent systems can be tuned to adjust the solvating power of the system for a particular diacetylenic monomer by varying the proportions of the solvent system components.

If desired, other liquids or solids can be included in the solvent system as will be, or will become, apparent to a person of ordinary skill in the art. Optionally, the specified solvent or solvents can comprise at least 50 percent by weight of the solvent system, the balance being the other liquids and water, if employed. The other liquids can be solvents or nonsolvents for the diacetylenic compound or compounds to be dissolved, and can for example be another of the liquids mentioned as solvent system components herein. Some embodiments of the invention employ solvent systems which are free of any dissolved or undissolved solids and can formulate solutions containing only a desired diacetylenic compound or compounds in addition to the solvent system.

Alternatively, or in addition, solid additives can be incorporated in the solvent system, provided they are not incompatible with the objectives of the invention, for example, a precipitation additive such as is described and claimed in U.S. Pat. No. 7,019,171 to Prusik et al.

Diacetylenic Solutions

Some embodiments of the invention include solutions of one or more diacetylenic monomers in one of the solvent systems described herein as suitable for the purpose. Further embodiments of the invention comprise solutions of the diacetylenic monomer in new solvent systems having a system solubility point in the defined solubility region.

The invention also includes solutions of the diacetylenic monomer or monomers in a solvent system embodiment of the invention in any desired proportion up to the limits of the solvating properties of the solvent system. For example the proportion of diacetylenic compound or compounds can be at least 1 percent, at least 4 percent or at least 7 percent by weight based upon the weight of the solution. For many purposes, high solubilities can be useful and the invention includes diacetylenic solution embodiments comprising at least about 7 percent by weight of the solution of dissolved diacetylenic compound. Some further embodiments of the invention comprise diacetylenic solutions comprising at least about 10 percent by weight of dissolved diacetylenic compound, based upon the weight of the solution.

Some examples of diacetylenic monomers that can be employed in the practice of the invention include any diacetylenic compound capable of providing a visual indication, such as a color change in response to exposure to an environmental condition enabling the condition to be indicated or monitored. Some diacetylenic compounds useful as diacetylenic monomers in the practice of the present invention can respond to temperature, humidity, ambient atmospheric chemical composition, environmental pressure, ambient radiation, another ambient condition or combinations of these parameters.

For example, diacetylenic compounds useful as indicator agents that provide an irreversible indication of cumulative thermal exposure and which may be employed as diacetylenic monomers in practicing the present invention are disclosed in the Patel, Preziosi and other patents cited herein. The disclosures of Patel U.S. Pat. No. 3,999,946 at column 4, line 13, to column 5, line 48 and of Preziosi et al. U.S. Pat. No. 4,788,151 at column 3, line 58, to column 4, line 62, are incorporated by reference herein. In the disclosures incorporated from these documents, references to "the invention", "preferred", "preferably" and the like are to be understood to refer to the invention of the respective cited patent rather than to the invention herein.

If desired, the diacetylenic monomer compound can be selected from the group consisting of: 2,4-hexadiyn-1,6-bis(alkylurea) compounds wherein the alkyl groups have from 1 to 20 carbon atoms; 2,4-hexadiyn-1,6-bis(alkylurea) compounds wherein the two alkyl groups are each independently ethyl, propyl, butyl, octyl-, dodecyl or octadecyl; the foregoing substituted alkyl urea compounds wherein the alkyl substituents are linear; and mixtures comprising any two or more of the foregoing diacetylenic compounds. The polymerizable diacetylenic monomer can be symmetrically substituted, if desired.

Useful in the practice of the invention are polymerizable diacetylenic compounds or monomers of structural formula

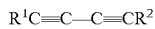

wherein each of $R^1$ and $R^2$ independently is an organic substituent compatible with providing the irreversible appearance change. For example, each of $R^1$ and $R^2$ can independently be —$R^4$NHCONHR$^3$ where $R^3$ is alkyl having from 1 to 20 carbon atoms, optionally ethyl, propyl, butyl, octyl, dodecyl or octadecyl and $R^4$ is alkyl having from 1 to 20 carbon atoms, for example, methylene, ethylene, propylene or butylene. If desired, $R^1$ and $R^2$ can each be $CH_2$—NHCONHR$^3$ and each $R^3$ independently can be a straight-chain or branched saturated alkyl group. Some of the foregoing compounds are useful as active components of ambient condition indicators, for example, time-temperature indicators.

Other diacetylenic compounds or monomers which can usefully be employed in the practice of the invention will be, or become, apparent to a person of ordinary skill in the art. Some further examples of diacetylenic compounds that can be employed include diacetylenic compounds that are sensitive to higher energy radiation but are relatively insensitive to ambient-thermal conditions such as 5,7-dodecadiyn-1,12 diol bis(n-octadecyl urethane, (also referenced "4DOD" herein) and 5,7-dodecadiyn-1,12 diol bis(n-butoxycarbonyl urethane.

Thus, the diacetylenic monomer can, if desired be a diacetylenic compound having the structural formula

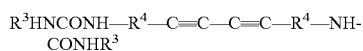

wherein each $R^3$ and $R^4$, independently, is as stated above.

In a further aspect, the invention provides a crystallized diacetylenic indicator agent having a crystal phase comprising a solid solution of, and/or co-crystallized from, a first diacetylenic compound and a second diacetylenic compound each of the first and the second diacetylenic compounds independently having the structural formula

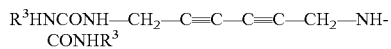

wherein each $R^3$ is a straight-chain or branched saturated alkyl group having from 1 to about 20 carbon atoms and can be the same or different.

Some specific examples of useful diacetylenic compounds comprise 2,4-hexadiyn-1,6-bis(ethylurea), 2,4-hexadiyn-1,6-bis(propylurea) and a co-crystallized mixture, or solid solution, of 2,4-hexadiyn-1,6-bis(ethylurea) and 2,4-hexadiyn-1,6-bis(propylurea).

The invention includes a time-temperature indicator comprising a diacetylenic active indicator agent having a crystal phase comprising at least one of a first and a second diacetylenic compound, each of the first and second diacetylenic compounds having the structural formula R—C≡C—C≡C—R, wherein the substituent R is —$CH_2NHCONHCH_2CH_3$ in the first compound and is —$CH_2NHCONH(CH_2)_2CH_3$ in the second compound and further comprising at least one non-acetylenic compound in the crystal phase, the at least one non-acetylenic compound optionally being at least one solvent.

Some examples of suitable diacetylenic monomers that can be employed in embodiments of diacetylenic solution according to the invention, and in other aspects of the invention, as described herein, include, ethyl-, propyl-, and octyl-substituted 2,4-hexadiyn-1,6-bis(alkylurea) compounds as well as co-crystallized mixtures and solid solutions of two or more of these compounds.

Recrystallization

Recrystallization of diacetylenic monomers from solution can often be a useful method of providing "fresh" active monomer that is polymer free, for providing new monomer crystal structures having desired reactivity, and for growing large crystals of the diacetylenic monomer. Known methods of processing diacetylenic monomers generally yield amorphous or crystalline powders the crystals in which have maximum dimensions which are too small for complete identification of the crystal structure by conventional X-ray crystallography.

Recrystallization processes can also be employed, or adapted, if desired, to purge a raw material of undesired polymeric material, for example by separating the polymer from a solution of the monomer by filtration, centrifugation or other suitable means.

As stated herein, care may be required in crystallizing or recrystallizing diacetylenic compounds from heated supersaturated solutions to avoid time-temperature induced polymerization. Problems can arise at lower temperatures, where polymerization might be less of a problem, owing to limited solubility of the diacetylenic monomer in known solvents and solvent systems at lower temperatures. Accordingly, there is a need for a method of growing larger crystals, for example crystals having a dimension greater than about 2 mm of pure diacetylenic compound from a supersaturated solution. Larger crystals having a dimension of at least about 5 mm or at least about 10 mm would also be desirable for some purposes.

Crystallized diacetylenic compounds according to the invention can be prepared by any suitable method for example by crystallizing the diacetylenic compound from a diacetylenic solution of the diacetylenic compound in a solvent system. The diacetylenic solution can be prepared by dissolving the diacetylenic compound in the solvent system or by another suitable method. If desired, the diacetylenic compound can comprise an unpurified crystallization product, Generally stated, the invention includes a method of recrystallizing a diacetylenic compound which method comprises heating a mixture of the diacetylenic compound in a solvent system for the diacetylenic compound at a temperature in the range of from about 50° C. to about 100° C., optionally on a heated water bath, to dissolve the diacetylenic compound in the solvent system and allowing the solution to cool without providing heat and without quenching to precipitate crystals of the diacetylenic compound.

One embodiment of the invention comprises a method of recrystallizing a diacetylenic monomer, for example a bisalkylurea diacetylenic monomer, the method comprising dissolving the diacetylenic compound in a suitable solvent providing a desired loading of solute, at an acceptable working temperature, and which does not react with the solute under the conditions employed. Any useful solute loading can be employed, for example, a solute loading of at least about 1 percent by weight of diacetylenic compound based on the weight of the solution. Higher loadings, for example at least about 4 percent or at least about 7 percent by weight, can be employed, if desired.

Heating can be employed to facilitate dissolution, if desired, for example heating to a temperature within about 5° C. of the boiling point of the solution. If desired, the solution can be refluxed at a temperature at or near its boiling point to vary the reactivity of the diacetylenic compound, for example as described and claimed in U.S. Pat. No. 6,924,148 to Prusik.

If desired, the raw solution can be filtered, centrifuged or otherwise processed to remove particles or molecules of polymerized material or other undesired solid material that may have been present in the raw diacetylenic monomer powder or solution.

EXAMPLE 3

Recrystallization

In accordance with one embodiment of the invention, the following procedure can be used to recrystallize a diacetylenic monomer, for example, 2,4-hexadiyn-1,6-bis(ethylurea), from the diacetylenic monomer solutions described herein, for example ethanol/water, or from other diacetylenic monomer solutions, as will be apparent to a person of ordinary skill in the art.

Preheat a water bath on a temperature controlled hotplate/stirrer to a process temperature of choice for example 90° C. For a 1% solution, add 0.4 grams raw 2,4-hexadiyn-1,6-bis(ethylurea) and 9.6 grams 1:3 parts water/ethanol by wt. (or other solvent of choice) to a 20 mL glass scintillation vial. The quantity of solute, for example 2,4-hexadiyn-1,6-bis(ethylurea), is varied according to the concentration desired.

Heat the vial at 90° C. in a water bath and stir with magnetic stirring bar. Observe the dissolution of 2,4-hexadiyn-1,6-bis(ethylurea) diacetylenic monomer. When no particles of 2,4-hexadiyn-1,6-bis(ethylurea) remain visible, switch off the heat and stirring and allow the water bath to cool. Crystals will slowly precipitate out of the solution.

When the water bath temperature has cooled to about 35° C., remove the vial from the bath and prepare a vacuum filtration set up with a 5 micron pore size polytetrafluoroethylene filter. Filter the crystal/solvent slurry, air-dry the product for 15 min, and then transfer it to a glass scintillation vial.

Collect the final product and place it in a freezer at about −30° C. If the crystals are still wet, as may be the case with a high boiling-point solvent, place the chilled crystals in a vacuum chamber (such as a FLEXI-DRY MP (trademark) lyophilizer at a pressure of <500 mTorr for about 1-2 hours and then return it to the freezer.

A significant portion of recrystallized 2,4-hexadiyn-1,6-bis(ethylurea) can be recovered utilizing the method of Example 3 by employing solutions of 4 percent and 7 percent 2,4-hexadiyn-1,6-bis(ethylurea) by weight, yielding long white needles of 2,4-hexadiyn-1,6-bis(ethylurea).

Another embodiment of recrystallization method according to the invention comprises a first step of rapidly cooling a hot diacetylenic monomer solution having a temperature of about 80° C. or higher to an intermediate temperature to limit possibly polymerization of the monomer. The method also comprises a second step of growing crystals of a desired size from the intermediate temperature by slow or moderate cooling to a lower temperature, for example room temperature or below. The intermediate temperature can be from about 30° C. to about 50° C., for example about 35° C. about 40° C., or other suitable temperature. Quenching with an immiscible solvent, or forced circulation or other suitable method can be used to speed cooling in the first step, if desired and a water bath or the like can be employed to limit cooling in the second step, if desired.

The invention includes a crystallized diacetylenic compound produced by any of the recrystallization methods described herein. Many temperature-sensitive diacetylenic compounds are constantly polymerizing, from the moment of crystallization at temperature-dependent rates. Under low-temperature storage conditions, for example from about −4° C. to about −30° C., the rate of polymerization may be so slow that little or no physical effects are apparent even after extended periods of time such as months or years. Higher polymerization rates at higher temperatures can, with appropriate compounds, lead to development of color or color change. As is known, this phenomenon is useful in time-temperature indicators such as the time-temperature indicators of the invention.

Accordingly, the crystallized diacetylenic compounds of the invention can, in some cases, comprise small amounts of polymerized diacetylenic compounds, for example, up to about 0.1 percent by weight, up to about 1.0 percent by weight or up to about 10 percent by weight, of the crystallized diacetylenic compound can comprise polymer.

Figure 11:
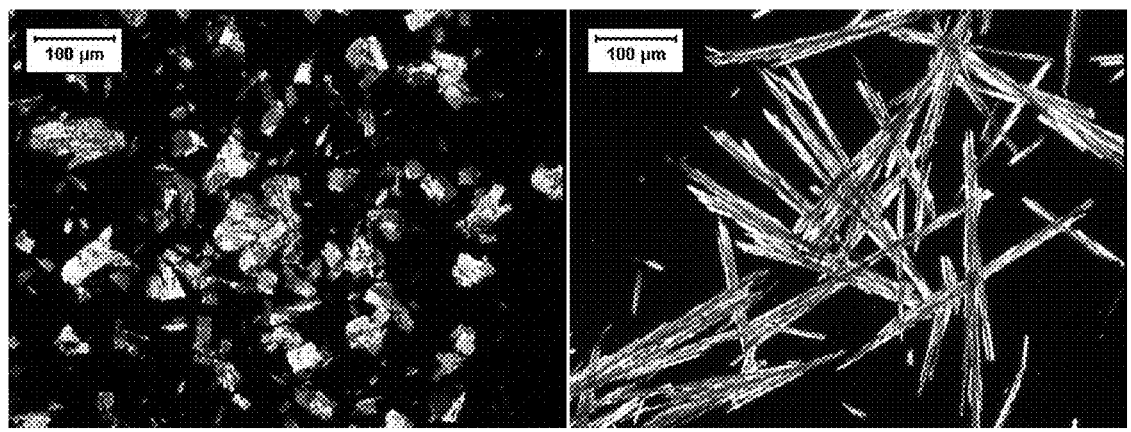
FIG. 11 shows two photomicrographs of two crystalline diacetylenic monomers, that on the left being of a known diacetylenic monomer and that on the right being of a diacetylenic monomer according to the invention.

The images shown in FIG. 11 are polarized optical microscope images of crystals of 2,4-hexadiyn-1,6-bis(ethylurea) grown from solutions in different solvents under different conditions. The small crystals on the left are obtained in conventional manner by recrystallization from hot acetic acid employing quenching with methanol to effect cooling. The larger crystals on the right are grown from a 25% water/ethanol mixture (a 1:3 mixture by weight) by cooling at about 1° C./min.

A 100 micron, 0.1 mm scale is shown in each photomicrograph for size estimation. Comparing the images, the product recrystallized from a water/ethanol mixture, pursuant to the invention, can be seen to comprise largely of regular, long white crystals many of which have dimensions of about 0.2 mm or greater. In contrast, the crystals on the left, precipitated from hot acetic acid, are more like a powder, being irregular in shape and relatively small, with few, if any, crystals larger than 0.1 mm and few, if any, needles being present.

Figure 12:
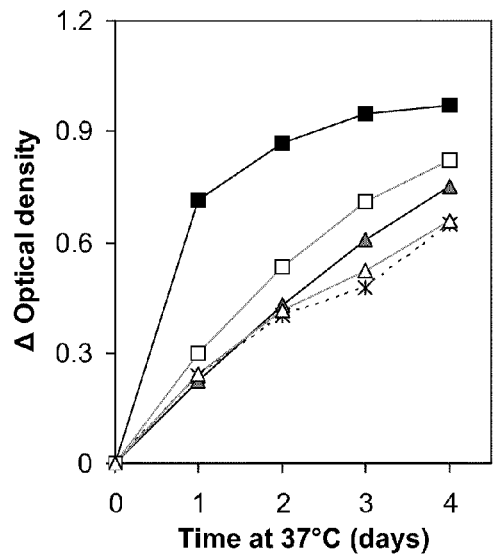
FIG. 12 is a graph showing the cumulative color-change response of a number of diacetylenic monomers exposed to one ambient temperature.
Figure 13:
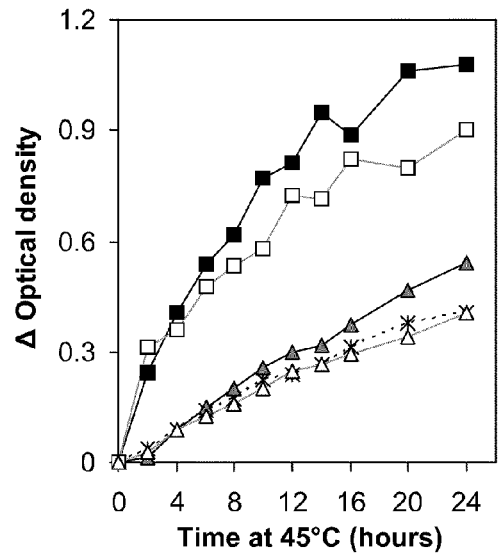
FIG. 13 is a graph showing the cumulative color-change response of the diacetylenic monomers referenced in FIG. 12, exposed to another ambient temperature.
Figure 14:
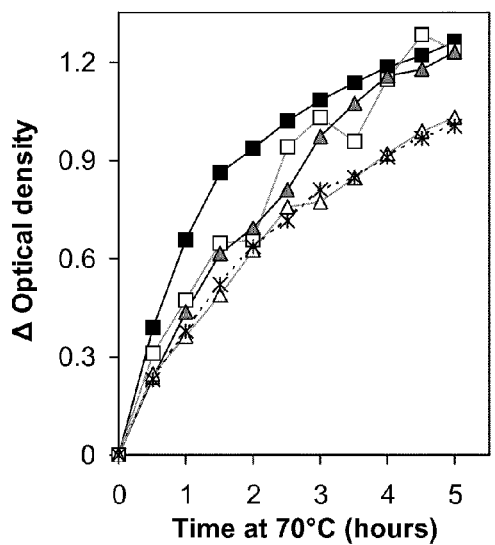
FIG. 14 is a graph showing the cumulative color-change response of the diacetylenic monomers referenced in FIG. 12, exposed to a third ambient temperature.

Samples of 2,4-hexadiyn-1,6-bis(ethylurea) recrystallized from a number of different solvent systems can be tested for their relative reactivities. For example, the ability of the diacetylenic monomer to change color in response to time-related exposure to an environmental condition, such as temperature exposure, can be tested, yielding results such as are shown in FIGS. 12-14, employing the method described in Example 4.

EXAMPLE 4

Comparative Color-Change Reactivities

Sample pellets are prepared from crystalline diacetylenic monomer powder using an E-Z Press 12-Ton Hydraulic Press and KBr Pellet Kit with 13 mm die set, as supplied by International Crystal Laboratories (Garfield, N.J.). Using about 300 mg powder, a pressure of 5 to 8 tons is applied for 2-3 minutes. Samples of 2,4-hexadiyn-1,6-bis(ethylurea) precipitated from dimethyl sulfoxide, methanol and a 4:1 by weight ethanol/water mixture are prepared. Pellets of raw 2,4-hexadiyn-1,6-bis(ethylurea) crystals ("KE raw"), precipitated from a solution in hot glacial acetic acid, using methanol as a precipitant, shortly after the 2,4-hexadiyn-1,6-bis(ethylurea) was synthesized, are included as controls.

While being handled by the edges, an individual pellet is placed in a transparent heat-seal bag, about 50 mm by 115 mm, vacuum sealed and placed into a heat-sealable foil pouch. The foil pouch is vacuum-sealed using a Fuji Impulse tabletop vacuum heat sealer. The sealed foil pouch containing the pellets is stored in a freezer at −30° C., or other suitable temperature, until ready for testing.

The heat-sealed foil pouch samples containing the pellets are placed in a water bath, for example a Huber circulating water bath, set to appropriate temperatures for example 37° C., 45° C. or 70° C., and aged for suitable measured time periods such as a few days at 37° C. or a few hours at 70° C. where the reaction proceeds more rapidly. The samples are weighted to keep them immersed in the water during the test. Timing is started immediately after each pouch is placed into the water bath. The pouch is removed at the end of the designated test period and its optical density is measured.

To measure optical density the pouch is briefly immersed in a second water bath set at 20° C. to quench the sample and prevent further color change during measurement. The foil pouch is cut open leaving the pellet inside the transparent heat-sealed bag. The reaction kinetics of the diacetylenic monomer are determined by measuring the cyan optical density (O.D.) of the aged pellets using an X-Rite 404 color reflection densitometer. The optical density can be measured on an arbitrary scale and used for comparative indications of color change reactivity.

In order to compensate for the thickness of the pellets, which are about 2 mm thick, when using the densitometer, the densitometer can be raised on to an elevated platform of corresponding height. Some results obtainable are shown in FIGS. 12-14.

FIG. 14 includes a key to the solvent systems for which possible test results are shown. This key is also applicable to FIGS. 12 and 13.

The graphs in FIGS. 12-14 plot measured color change, as changes in optical density of samples, over time in days at 37° C., 45° C. or 70° C. respectively and can be generated by the method described in Example 4. The graphs show significant differences in the reactivities of the diacetylenic monomers tested, according to the solvent employed to recrystallize the monomer.

Notably, as may be seen in FIG. 12, at 37° C. 2,4-hexadiyn-1,6-bis(ethylurea) crystallized from pyridine (black squares) exhibits faster color change kinetics than does the raw product (stars) and also shows a faster rate of color change than the product obtained from any other solvent in the test. In addition, the pyridine product has a lower activation energy than the raw product, for example about 19 kcal/mol compared with 23 kcal/mol for the raw control. Similar effects are manifest at 45° C., as shown in FIG. 13, and to a lesser extent at the higher temperature of 70° C., as shown in FIG. 14.

2,4-hexadiyn-1,6-bis(ethylurea) recrystallized from DMSO displays modestly faster reactivity than raw 2,4-hexadiyn-1,6-bis(ethylurea) at 37° C., as shown in FIG. 12. However at 45° C., this effect is significantly more pronounced, as can be seen in FIG. 13 where the reactivity profile of the DMSO product is close to that of the pyridine product and significantly differentiated from the other products tested.

As shown in FIG. 14, at the higher temperature of 70° C. similar relative results can be obtained but there is less differentiation between products over the shorter time scale.

Overall, the several samples of diacetylenic monomer recrystallized from the solvents listed displayed visual response reactivities comparable with or faster than the raw product suggesting they can be employed as active elements in environmental condition indicators. The variation in reactivity from that of the raw product can give the formulator more options for correlating an indicator with the responses of a host product to be monitored.

The new solvent systems identified or provided by the invention for preparing diacetylenic monomer solutions provides processing and recrystallization choices that can be useful in a number of ways. For example, the diacetylenic monomer solutions may in some cases be useful as indicator agents, or elements, for example when applied to a substrate, or in other ways. As described, one or more solutions can be used to provide new crystal forms of diacetylenic monomers, for example larger crystals useful for X-ray or other analysis.

X-Ray Crystallographic Analysis

To facilitate understanding of and modeling of possible diacetylenic polymerization reaction mechanisms and to help identify useful new diacetylenic monomer processing methods it can be useful to have more structural information about crystallized diacetylenic monomers. Pursuant to the invention, such crystallographic information can be used to differentiate between crystallized forms of a diacetylenic compound to identify forms that may be more useful than others for a particular application, for example for time-temperature, irradiation dosage or other ambient condition indicators or the like, where indicator performance may be sensitive to crystal structure.

Accordingly, some further embodiments of the invention comprise evaluation of crystalline powdered samples of diacetylenic monomers of interest by X-ray diffraction or other suitable technique. Crystalline powders useful for crystallographic analysis can generally be obtained by rapid quench or another fast cooling method from hot solutions of a diacetylenic monomer in acetic acid or another one of the solvent systems described or suggested herein, or from a solution in which the diacetylenic monomer has been synthesized. In general, it appears that X-ray diffraction studies can be made on the monomer without undue interference from minor amounts of polymer that may be present or may be generated by the study.

In one exemplary method of X-ray analysis, a powdered sample of a crystallized diacetylenic monomer material to be analyzed is withdrawn from storage in a freezer, placed on a holder, and then characterized using X-rays of a desired fixed wavelength.

The angular variation of the intensity of diffracted radiation is recorded using a goniometer. The recorded data are then analyzed in terms of the diffraction angle, and the wavelength of the radiation used for crystal diffraction, to evaluate inter-atomic spacings, or d-values in the crystal structure in Angstrom units, "Å" (1 Å=$10^{-10}$ m). The distances between planes of atoms that constitute a sample can be calculated from the goniometer data by applying Bragg's Law, in known manner. When values of X-ray diffraction Bragg angle 2θ are mentioned herein and the X-ray radiation is not specified, the X-ray radiation employed is to be understood to have a wavelength of about 1.54 Å.

The characteristic set of d-spacings generated in a typical X-ray scan generally provides a unique "fingerprint" of the material present in the crystal sample. When suitably interpreted, by comparison with standard reference patterns and measurements, this "fingerprint" can often permit unambiguous identification of a sample material.

EXAMPLE 5

Structural Analysis of Powdered Crystal (Ethylurea Compound)

Experimental X-ray diffraction patterns for a diacetylenic compound of interest, in this case powder crystals of raw 2,4-hexadiyn-1,6-bis(ethylurea) precipitated immediately after synthesis from a solution of acetic acid, using methanol, for example generally as described in Example A of Preziosi et al. U.S. Pat. No. 4,788,151, are generated using a Rigaku ULTIMA (trademark) diffractometer, providing Cu K radiation at a wavelength "λ" of 1.54056 Å. Some results obtainable are shown in the lowermost diffraction pattern illustrated in FIG. 15.

Figure 15:
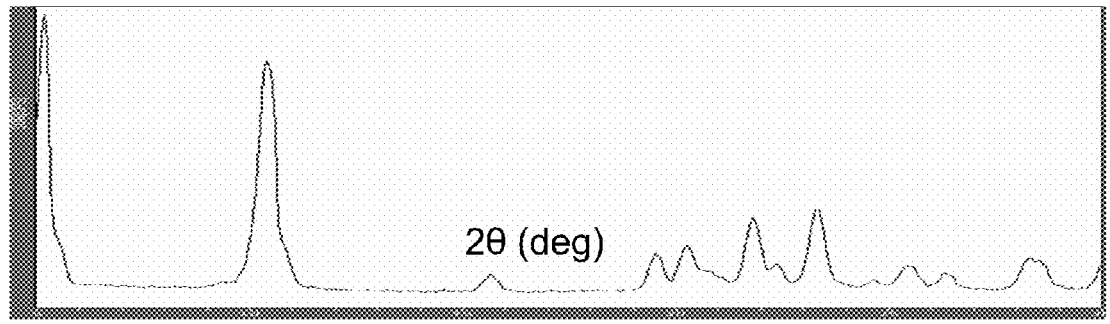
FIG. 15 is an X-ray diffraction pattern showing the results of characterization of a first crystalline diacetylenic monomer.

The data shown in FIG. 15 are plotted as dependence of the square root of diffracted beam intensity on the vertical axis versus 2θ degrees on the horizontal axis, "θ" being the angle of incidence of the X-ray beam. The same axis designations are used for all X-ray diffraction patterns shown in the drawings. Unless the context indicates otherwise, references herein to a diffraction angle are to be understood to mean "2θ".

Referring to FIG. 15, a notable feature of the diffraction pattern for raw powdered 2,4-hexadiyn-1,6-bis(ethylurea) is the presence of two high intensity peaks near 2θ values of about 5.18 degrees and 10.39 degrees. These two intense peaks are narrow and rise sharply to intensities many times higher than background. The 2θ values at which the peaks are found correspond with d values of 17.06 and 8.51 Å, respectively, according to Bragg's law. For convenient reference, these two peaks can be indexed as 001 and 002 reflections of the diacetylenic monomer crystal lattice.

EXAMPLE 6

Structural Analysis of Powdered Crystal (Various Solvents)

Example 5 is repeated using crystals of 2,4-hexadiyn-1,6-bis(ethylurea) recrystallized from a number of different solvents, identified as follows:

| Sample A | acetic acid |
|---|---|
| Sample C | 1:4 parts by weight water in dimethyl sulfoxide |
| Sample E | 1:4 parts by weight water in ethyl alcohol |
| Sample F | 1:4 parts by weight water in isopropyl alcohol | under relatively fast cooling conditions yielding powdery crystal precipitates and designed to avoid undue spontaneous polymerization. Some results obtainable are shown in the diffraction patterns illustrated in FIG. 16.

Figure 16:
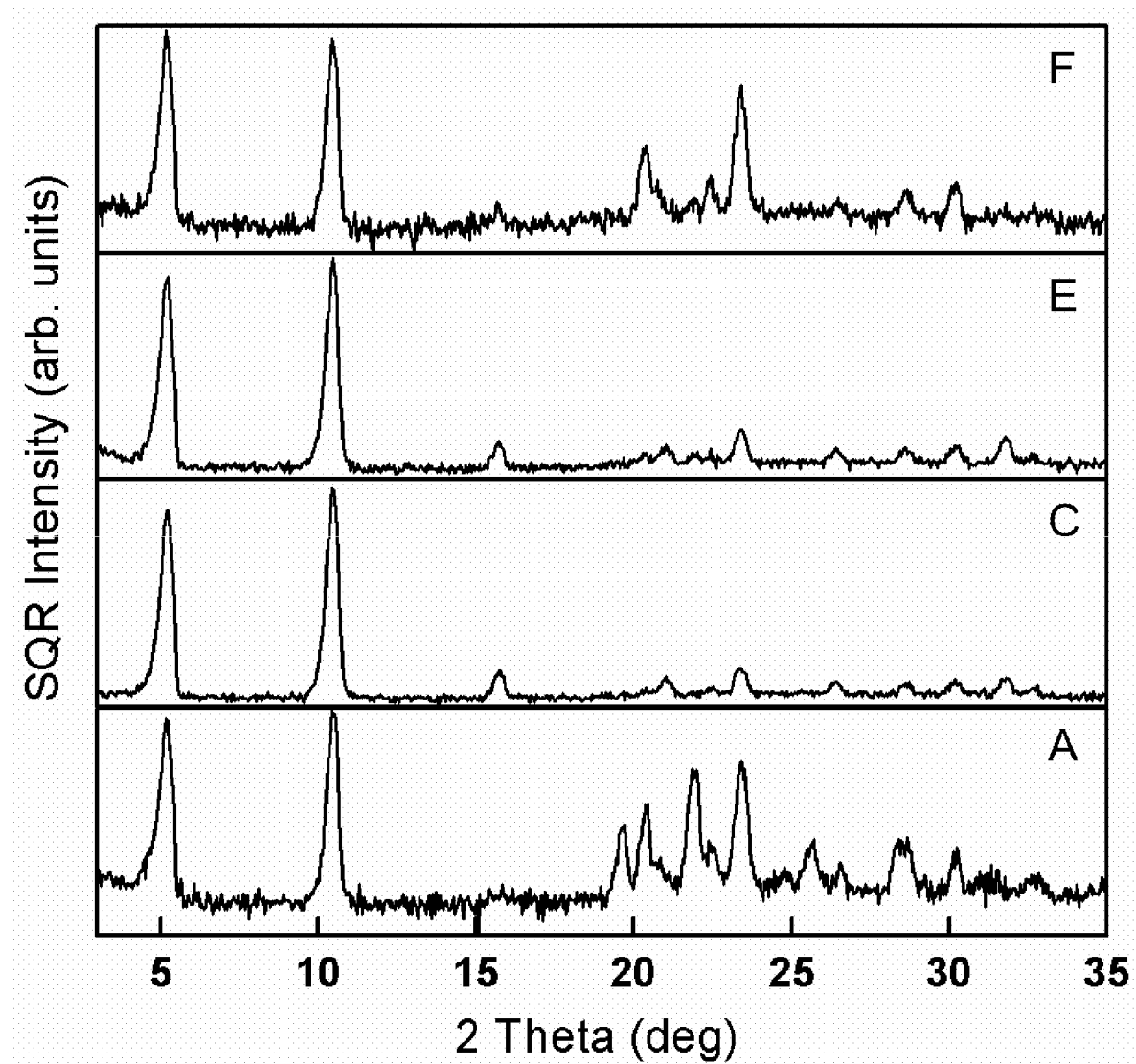
FIG. 16 is a set of X-ray diffraction patterns showing the results of characterization of a number of additional crystalline diacetylenic monomers.

Referring to FIG. 16, it can be seen that the positions and relative intensities of the 001 and 002 peaks in a low-angle region, where 2θ is from about 4 degrees to about 12 degrees, are similar for all investigated samples. This fact may suggest that each of the crystal structures has comparable inter-planar separations in the associated crystal plane directions. As described herein, unless the context indicates otherwise, 2θ angles are characterized using copper Kα radiation at about 1.542 Å.

In addition, the various diffraction pattern profiles reveal significant differences in a high angle region where 2θ is from about 19 degrees to 24 degrees. In particular the high angle diffraction pattern can be seen to vary substantially according to the recrystallization solvent employed. For example, the diffraction pattern for the sample of the known acetic acid product, Sample A, exhibits four distinct high intensity peaks in the high angle range where 2θ is from about 19 degrees to about 24 deg. The pattern for the water/isopropyl alcohol sample, Sample F exhibits only two pronounced high intensity peaks in the high angle range, also in the range where 2θ is from about 19 degrees to about 24 degrees. In contrast, the diffraction patterns for 2,4-hexadiyn-1,6-bis(ethylurea) recrystallized from dimethyl sulfoxide product, Sample C, and water/ethyl alcohol Sample E lack significant high intensity peaks in the high angle range of 2θ.

Giving the height of the vertical axis shown in FIG. 16 a value of 1, it can be determined by measurement of the figure that Sample A exhibits four high intensity peaks in the high angle range of from about 19 degrees to about 24 degrees which exceed a value of 0.4. Sample F exhibits two high intensity peaks in the high angle range of from about 19 degrees to about 24 degrees which exceed a value of 0.4, while neither Sample C nor Sample E exhibits any.

Figure 17:
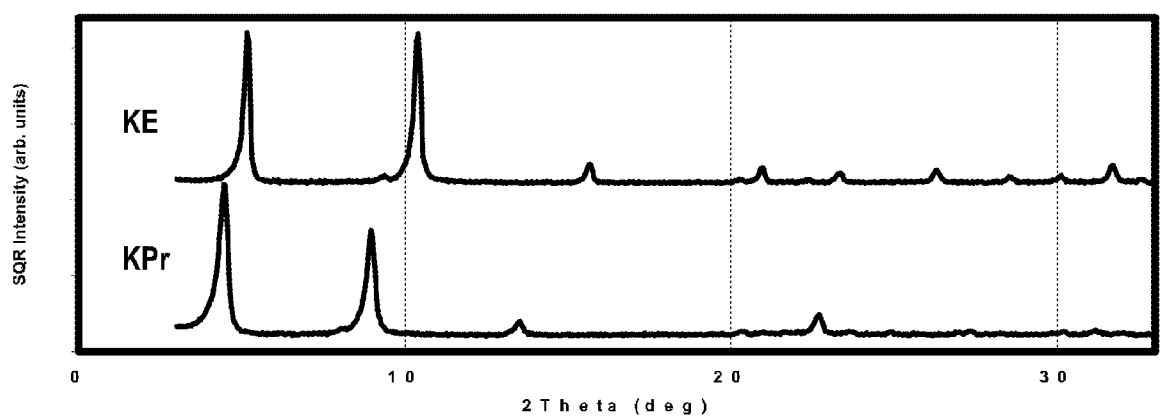
FIG. 17 shows two X-ray diffraction patterns showing the results of characterization of two crystalline diacetylenic monomers precipitated from diacetylenic solutions according to the invention.

The X-ray diffraction data shown in FIGS. 15-17 and Table 4 are exemplary of data obtainable for 2,4-hexadiyn-1,6-bis(alkylurea) compounds. The invention includes novel crystallized diacetylenic compounds having X-ray diffraction data as shown in the accompanying figures or as described herein or having peaks or other properties within the angular or other ranges described herein.

EXAMPLE 7

Structural Analysis of Powdered Crystal (Ethanol/Water)

Example 5 is repeated using crystals of 2,4-hexadiyn-1,6-bis(ethylurea) ("KE") and 2,4-hexadiyn-1,6-bis(propylurea) ("KPr") recrystallized from a 95/5 percent weight for weight ethyl alcohol/water solution with relatively rapid cooling from a temperature near the boiling point of the mixture under relatively fast cooling conditions to yield powdery crystal precipitates and attempt to avoid undue spontaneous polymerization. Some results obtainable are shown in the diffraction patterns illustrated in FIG. 17 where the patterns for the respective diacetylenic monomers are labeled "KE" and "KPr".

Referring to FIG. 17, the diffraction pattern for 2,4-hexadiyn-1,6-bis(ethylurea) recrystallized from 5:95 water/ethanol can seen to be similar to the diffraction pattern for recrystallization from 1:4 water/ethanol shown in FIG. 16.

The diffraction pattern for 2,4-hexadiyn-1,6-bis(propylurea), labeled "KPr", is generally similar to that for 2,4-hexadiyn-1,6-bis(ethylurea) with the difference that the two low angle high intensity peaks are shifted downwardly to 2θ angles of about 4 degrees and 9 degrees, respectively. The 2,4-hexadiyn-1,6-bis(propylurea) pattern also lacks high intensity peaks in the high angle range.

Some measurable 2θ values, in degrees, at which low angle high intensity peaks, indexed 001 and 002 can be found together with corresponding calculated d values, in Angstroms, for 2,4-hexadiyn-1,6-bis(ethylurea) and 2,4-hexadiyn-1,6-bis(propylurea), are shown in Table 4, below.

TABLE 4

Measurable 2θ, and d-values for (001) and (002) peaks of KE and KPr

| Compound | $2\Theta_{(001)}$, deg | $d_{(001)}$, Å | $2\Theta_{(002)}$, deg | $d_{(002)}$, Å |
|---|---|---|---|---|
| KE | 5.16 | 17.112 | 10.4 | 8.499 |
| KPr | 4.44 | 19.885 | 8.96 | 9.861 |

Referring to Table 4, both crystallized compounds exhibit a 002 high intensity peak is at a 2θ angle which is approximately twice the 2θ angle of its 001 high intensity peak. The corresponding d spacings show the inverse relationship, namely approximately 1:2. In each case, the 001 and 002 high intensity peaks can be understood to have a harmonic relationship. $d_{(001)}$ for KPr (2,4-hexadiyn-1,6-bis(propylurea)) is about 16% larger than $d_{(001)}$ for KE (2,4-hexadiyn-1,6-bis(ethylurea)). This difference can be attributed to the difference in length of the two molecules.

As stated above, a crystal of a 2,4-hexadiyn-1,6-bis(alkylurea) compound can exhibit an X-ray diffraction pattern comprising two high intensity peaks at low 2θ diffraction angles of less than 12 degrees and the pattern can comprise less than four high intensity peaks at high 2θ diffraction angles in the range of from about 19 degrees to about 24 degrees, when characterized using X-rays at a wavelength of about 1.54 Å.

In one embodiment of the invention, the X-ray diffraction pattern of the crystal lacks high intensity peaks at high 2θ diffraction angles in the range of from about 19 degrees to about 24 degrees. One of the two high intensity peaks at low 2θ diffraction angles can be at an angle in the range of from about 4 degrees to about 6 degrees and the other can be at an angle in the range of from about 8 degrees to about 12 degrees.

The crystal of a 2,4-hexadiyn-1,6-bis(alkylurea) compound can exhibit a d spacing corresponding with the high intensity peak at an angle in the range of from about 4 degrees to about 6 degrees. This spacing can be half the value of the d spacing corresponding with the high intensity peak at an angle in the range of from about 8 degrees to about 12 degrees. In some cases, the two high intensity peaks at low $2\theta$ diffraction angles of less than about 12 degrees can have a harmonic relationship.

To provide more detailed information than can usually be obtained from powder X-ray crystallography, structural characterization of a single crystal of the diacetylenic monomer under study is desirable. An exemplary procedure, and the results obtainable are described in Example 8 below.

EXAMPLE 8

Structural Analysis of a Single Crystal (Ethylurea Compound)

A sample large enough for structural characterization of a single crystal of a diacetylenic monomer compound, using 2,4-hexadiyn-1,6-bis(ethylurea) by way of example, is obtained by crystallization from a 1:4 by weight water/ethanol solution following the recrystallization method described in Example 3. One embodiment of crystal has the shape of a needle and exhibits a well-defined growth direction.

Structural characterization can be effected by employing a Leica MZ7 polarizing microscope to identify a suitable specimen from a representative sampling of materials using any suitable procedure, an example of which follows. The identified specimen is attached to a nylon loop which is fashioned to a copper mounting pin. The mounted crystal is then placed in a cold nitrogen stream (Oxford) maintained at 110° K.

A Bruker D8 GADDS general purpose three-circle X-ray diffractometer is employed for sample screening and data collection. The goniometer is controlled using GADDS software suite (Microsoft Win 2000 operating system). The sample is optically centered with the aid of a video camera so that no translations are observed as the crystal is rotated through all positions. The detector is set at 50 mm from the crystal sample (MWPC Hi-Star Detector, 512×512 pixel). The X-ray radiation employed is generated from a Cu sealed X-ray tube ($K_\alpha$=1.54184 Å with a potential of 40 kV and a current of 40 mA) and filtered with a graphite monochromator in the parallel mode (175 mm collimator with 0.5 mm pinholes).

A rotation exposure is taken to determine crystal quality and the X-ray beam intersection with the detector. The beam intersection coordinates are compared to the configured coordinates and changes are made accordingly. If the rotation exposure indicates acceptable crystal quality, unit cell determination can be undertaken. Sixty data frames are taken at widths of 0.5° with an exposure time of 10 seconds. Over 200 reflections are centered and their positions are determined. These reflections are used in an auto-indexing procedure to determine the unit cell. A suitable cell is found, refined by nonlinear least square and Bravais lattice procedures and the results are recorded. The unit cell is verified by examination of the hkl overlays on several frames of data, including zone photographs. No super-cell or erroneous reflections should be observed.

After careful examination of the unit cell, a standard data collection procedure is initiated. This procedure comprises collection of one hemisphere of data using omega scans, involving the collection over 5000 0.5° frames at fixed angles for $\phi$, $2\theta$, and $\chi$ ($2\theta$=$-28$ °, $\chi$=$54.73°$, $2\theta$=$-90°$, $\chi$=$54.73°$), while varying omega. Additional data frames are collected to complete the data set. Each frame is exposed for 10 sec. The total data collection is performed for a duration of approximately 48 hours at 110° K. No significant intensity fluctuations of equivalent reflections are observed. After data collection, the crystal is measured carefully for size, morphology and color.

EXAMPLE 9

Structural Analysis of a Single Crystal (Propylurea Compound)

A sample large enough for structural characterization of a single crystal of 2,4-hexadiyn-1,6-bis(propylurea) ("KPr") is obtained by crystallization from a 1:4 by weight water/ethanol solution following the recrystallization method described in Example 3 using a similar quantity of 2,4-hexadiyn-1,6-bis(propylurea) in place of 2,4-hexadiyn-1,6-bis(ethylurea).

Crystals suitable for characterization having the shape of a needle and exhibiting a well-defined growth direction are obtained. One such suitable crystal is characterized by X-ray analysis in accordance with the method described in Example 8.

Crystallized Diacetylenic Compounds

The invention includes crystallized diacetylenic compounds having a triclinic or another crystal structure.

Exemplary single crystal structural data obtainable by the method of Example 8 for 2,4-hexadiyn-1,6-bis(ethylurea) grown from 1:4 water/ethanol are shown in Table 5.

TABLE 5

| Data for 2,4-hexadiyn-1,6-bis(ethylurea) grown from 1:4 water/ethanol | | | |
|---|---|---|---|
| Crystal system | Triclinic | | |
| Space group | P-1 | | |
| Unit cell dimensions | a = 4.2479(4) Å | | $\alpha$ = 88.966(7)° |
|  | b = 4.6199(5) Å | | $\beta$ = 84.663(6)° |
|  | c = 16.5577(18) Å | | $\gamma$ = 81.408(10)° |
| Volume | 319.90(6) Å$^3$ | | |
| Density (calculated) | 1.299 g/cm$^3$ | | |
| Crystal size | 0.25 × 0.04 × 0.01 mm$^3$ | | |

It can be noted that the unit cell parameter c, at 16.6 Å, as is determinable from a single crystal experiment, is smaller than the value obtainable from powder diffraction which is about 17.06 Å. This may be owing to different conditions of temperature or the like, or because the broad peaks obtainable in powder diffraction patterns make precise determination of d values difficult, or for other reasons.

Exemplary single crystal structural data obtainable by the method of Example 9 for 2,4-hexadiyn-1,6-bis(propylurea) grown from 1:4 water/ethanol are shown in Table 6.

TABLE 6

| Data for 2,4-hexadiyn-1,6-bis(propylurea) grown from 1:4 water/ethanol | | |
|---|---|---|
| Crystal system | Monoclinic | |
| Space group | P2$_1$/a | |
| Unit cell dimensions | a = 8.477 Å | $\alpha$ = 90°. |
|  | b = 4.594 Å | $\beta$ = 91.960(7)°. |
|  | c = 19.10 Å | $\gamma$ = 90°. |

TABLE 6-continued

Data for 2,4-hexadiyn-1,6-bis(propylurea) grown from 1:4 water/ethanol

| | |
|---|---|
| Volume | 743.4 Å$^3$ |
| Z | 2 |
| Density (calculated) | 1.244 g/cm$^3$ |
| Crystal size | 0.50 × 0.04 × 0.01 mm$^3$ |

Tables 9-12 which appear at the end of this specification, immediately before the claims, illustrate additional data obtainable by the method of Example 9.

When characteristic data for 2,4-hexadiyn-1,6-bis(ethylurea) ("KE") and 2,4-hexadiyn-1,6-bis(propylurea) ("KPr") are selected from Tables 5 and 6 and are compared as shown in Table 7, the overall structures of the two compounds have significant differences.

TABLE 7

Comparison of Select Data for KE and KPr

| | Space Group | a (Å) | b (Å) | c (Å) | α (°) | β (°) | γ (°) |
|---|---|---|---|---|---|---|---|
| KE | P-1 | 4.248 | 4.620 | 16.558 | 88.97 | 84.66 | 81.41 |
| KPr | P2$_1$/a | 8.447 | 4.594 | 19.100 | 90 | 91.96 | 90 |

Thus, although both diacetylenic compounds exhibit primitive centering space group designation "P", 2,4-hexadiyn-1,6-bis(ethylurea) has a triclinic structure with only a single center of symmetry, sometimes designated "$\bar{1}$". In contrast, KPr has a monoclinic structure and belongs to the space group P2$_1$/a, with a 2$_1$ screw axis and an a-glide plane, although it also has a single center of symmetry $\bar{1}$ ("one bar"). These features double the length of the a-axis and the number of molecules per cell.

A space group can be useful to describe the way in which molecules pack. A combination of unit cell parameters and atomic coordinates can indicate how the molecules are arranged in space in a crystal of a complex compound such as a diacetylene monomer. The molecular spatial arrangement in the crystal can be useful for describing or predicting the potential reactivity of a diacetylenic compound in an environmental condition indicator such as a time-temperature indicator.

As is known in the art, the triclinic space group comprises two structures, P1 and P$\bar{1}$ ("pee-one-bar" or P1 (bar)). The monoclinic space group comprises thirteen structures including structure P2$_1$/a. One source of information on space groups can be found on the internet at img.chem.ucl.ac.uk/sgp/mainmenu.htm.

Notwithstanding the above-described differences, further study of the available data can show that the crystal structures of 2,4-hexadiyn-1,6-bis(ethylurea) and 2,4-hexadiyn-1,6-bis(propylurea) have similarities with regard to characteristics relevant to polymerizability, for example, as is illustrated in Table 8 below.

TABLE 8

Comparison of Further Data for KE and KPr

| Compound | C1-C4 (Å) | d$_1$ (Å) | S (Å) | Y$_1$ (degree) | Hydrogen bonding? | H—O bond distance (Å) |
|---|---|---|---|---|---|---|
| KE, b-axis | 3.596 | 4.620 | 3.520 | 49.45° | In-plane | 2.095, 2.223 |
| KPr, b-axis | 3.490 | 4.594 | 3.451 | 47.86° | In-plane | 2.007, 2.072 |

Referring to Table 8, the long unit cell axis is the c-axis, the C$_1$-C$_4$ distance is the distance between a diyne carbon atom in one molecule and the closest diyne carbon atom in a neighboring molecule. Numbering the carbon atoms from 1 to 4 along the diyne group, the closest neighbor to the C1 carbon of one molecule is the C4 carbon of its neighbor. d$_1$ is the center-to-center separation between neighboring molecules which is greater than the C1-C4 distance. "S" is the perpendicular distance between adjacent diacetylene rods. γ$_1$ (Y$_1$ in Table 8) is the angle between the short b-axis and the diacetylene rod axis and the short b-axis is believed to be the reaction direction.

Despite differences in overall structure, it appears from the Table 8 data that the structures of 2,4-hexadiyn-1,6-bis(propylurea) and 2,4-hexadiyn-1,6-bis(ethylurea) structures are similar in the reaction direction as is further described herein.

Figure 18:
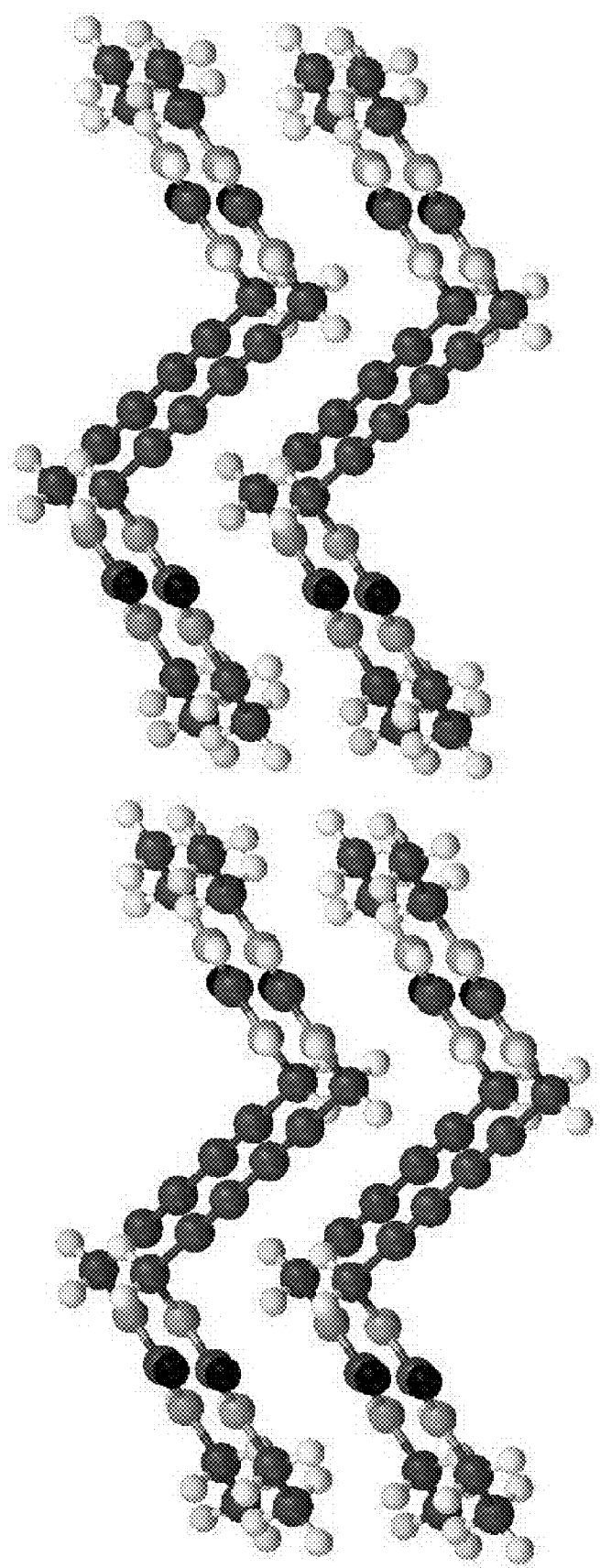
FIG. 18 is a perspective view of a model of crystal structure for a first diacetylenic monomer derivable from X-ray diffraction data.
Figure 19:
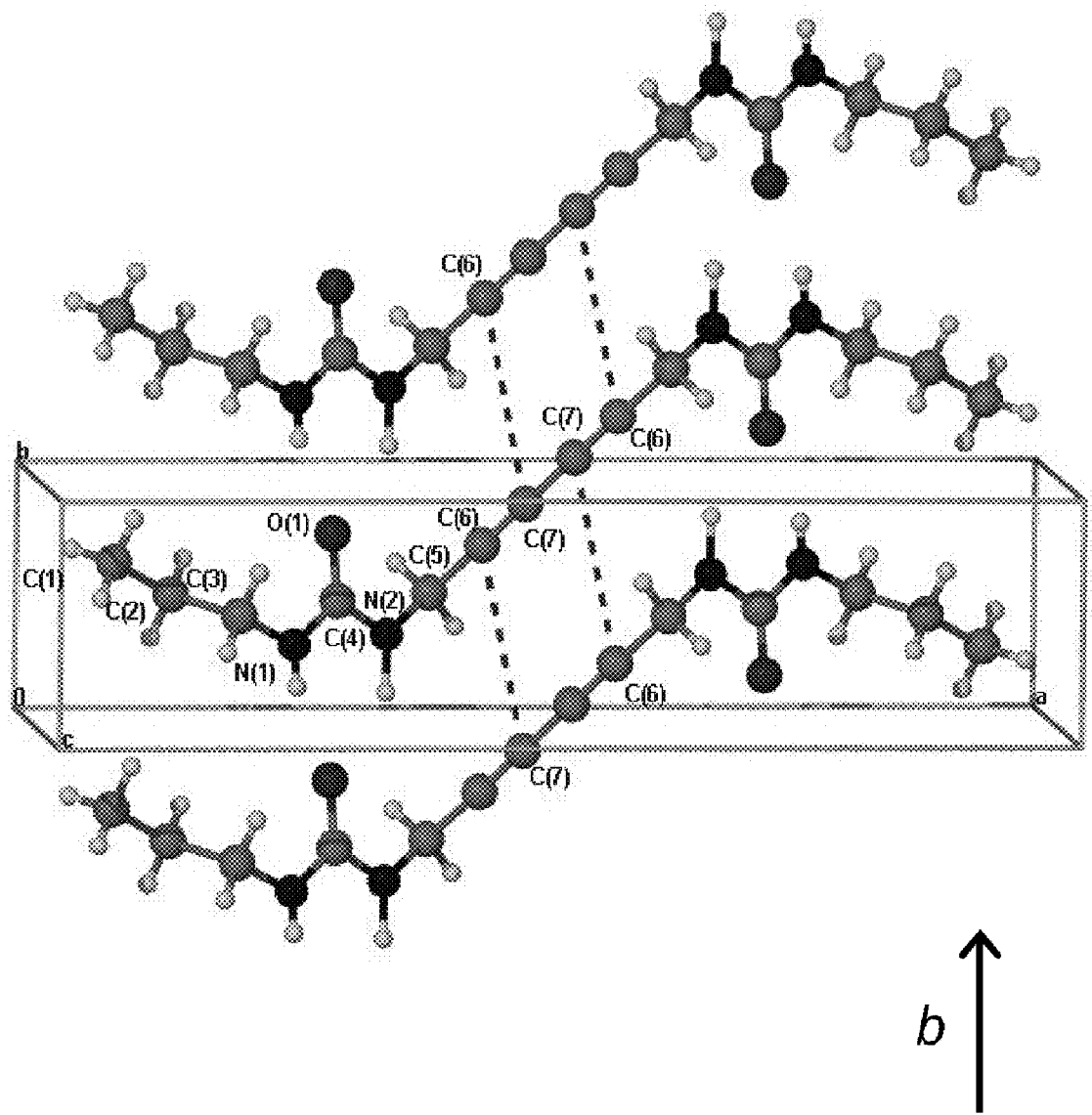
FIG. 19 is a perspective view of a model of crystal structure for a second diacetylenic monomer derivable from X-ray diffraction data.

One possible model of a crystal structure for 2,4-hexadiyn-1,6-bis(ethylurea) derivable from the data herein is shown in FIG. 18. A comparable model for a crystal structure for 2,4-hexadiyn-1,6-bis(propylurea) is shown in FIG. 19. These structures are consistent with available structural information for compounds in the diacetylene family.

In FIG. 19, it can be seen that the C(7) carbon atom of one molecule of 2,4-hexadiyn-1,6-bis(propylurea) is closely aligned with the C(6) carbon atom of a neighboring molecule of 2,4-hexadiyn-1,6-bis(propylurea). In FIG. 19, the carbon atoms are numbered C(1) to C(7) from each end of the molecule to the center of the molecule. A horizontal rectangular box indicates a unit cell with an origin at the far lower left corner of the cell the "a" axis extending from the origin to the right, the "b" axis extending upwardly and the "c" axis extending forwardly, referring to the plane of the paper or other medium in which FIG. 19 is rendered.

In the models shown in FIGS. 18 and 19, based upon the single crystal structural data described above, the diacetylenic monomer molecules have a center-to-center separation, referring to the geometric centers of adjacent unit cells of the crystal, of less than 4.7 Å. Also, the center-to-center separation is in a direction wherein solid-state polymerization can occur.

Figure 20:
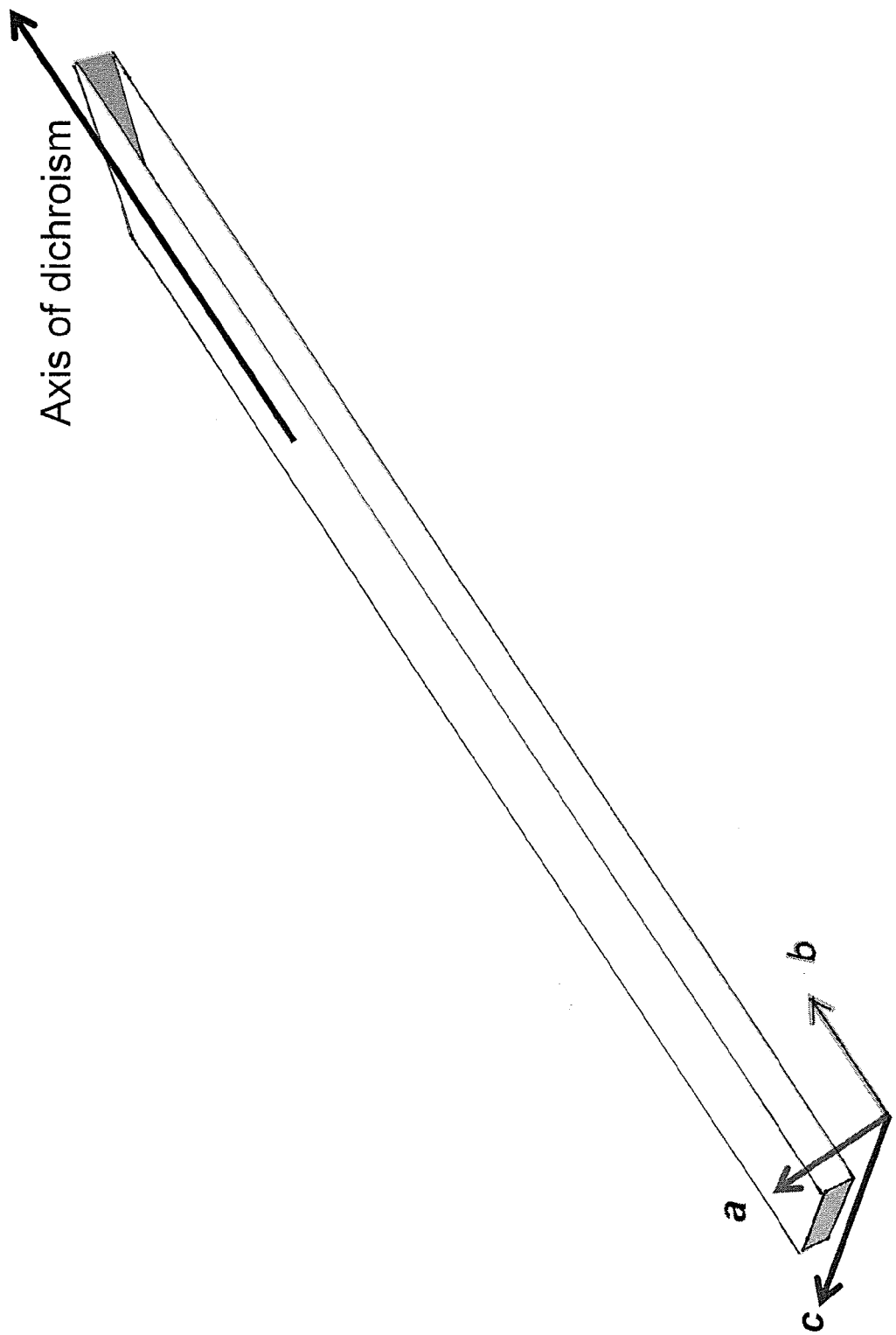
FIG. 20 shows schematically the orientation of crystal axes in relation to a crystal of a diacetylenic monomer.

FIG. 20 illustrates the relationship between the polymerization direction and the needle axis of a needle-shaped crystal of a polymerizable diacetylenic compound. The single crystal illustrated in FIG. 20 is shown schematically with a rectangular cross-section and the crystal axes (a), (b) and (c) are shown at the lower-left hand end of the crystal, as viewed in the figure.

The illustrated orientation of the diacetylenic monomer molecules in relation to the crystal axes is apparent from the marked arrow in FIG. 19 which shows the direction of the short crystallographic axis b.

As may be seen from FIGS. 19 and 20, the crystallographic short axis (b) is the needle axis for 2,4-hexadiyn-1,6-bis(propylurea) and possibly also for 2,4-hexadiyn-1,6-bis(ethylurea).

As is marked on the arrow in the figure, FIG. 20 shows that the axis of dichroism is believed to be parallel to the needle axis in both 2,4-hexadiyn-1,6-bis(propylurea) and 2,4-hexadiyn-1,6-bis(ethylurea). Hence, it can be concluded that the direction of polymerization, in the crystals of both compounds, is along the needle axis. The axis of dichroism is the direction in which coloration may become apparent when the monomer polymerizes.

Pursuant to model structures such as are described herein, the invention includes crystallized diacetylenic compounds comprising hydrogen bonds between neighboring polymerizable diacetylenic molecules and the hydrogen bonds can extend in a direction to permit 1,4-addition polymerization between two neighboring polymerizable diacetylenic molecules. If desired, a hydrogen bond can extend between each of two —NH— groups in a urea group on one polymerizable diacetylenic molecule and one =C=O group on a neighboring polymerizable diacetylenic molecule.

In general, the diacetylenic compound can be symmetrically substituted, and when crystallized can have a crystal structure wherein the diacetylene compound has a center of symmetry and no axes or planes of symmetry exist which structure corresponds to a triclinic crystal structure. Some aspects of the invention comprise diacetylenic compounds having a centrosymmetric crystal phase with unit cell parameters of a=about 4.2 Å, b=about 4.6 Å, c=about 16.5 Å, α=about 89° β=about 85°, and γ=about 81° and, optionally, a triclinic structure. It will be understood by a person of ordinary skill in the art that the particular choice of unit cell to represent the crystal structure for a triclinic or a monoclinic crystal may not be unique, and that other unit cells can be employed if desired, as may be determined by selection of the cell axis or other factors. Such other possible unit cells can be mathematically derived from a particular described or selected unit cell using known methods and are to be understood to be inherently included by providing information regarding a particular unit cell.

The invention includes a crystallized diacetylenic compound, 2,4-hexadiyn-1,6-bis(ethylurea), having the structural formula

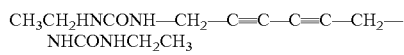
CH$_3$CH$_2$HNCONH—CH$_2$—C≡C—C≡C—CH$_2$—NHCONHCH$_2$CH$_3$ and having a triclinic crystal structure, which can have the above-stated unit cell parameters.

The proportion of the crystallized diacetylenic compound that comprises a crystallized diacetylenic compound having a triclinic crystal structure can be selected from the group consisting of at least about 50 percent, at least about 80 percent and at least about 90 percent, the proportions being by weight based upon the total weight of diacetylenic compound.

The crystallized diacetylenic compound can have any desired purity, for example a purity in a range selected from the group of ranges consisting of: at least about 90 percent by weight pure; at least about 95 percent by weight pure; at least about 98 percent by weight pure; at least about 99 percent by weight pure; and at least about 99.8 percent by weight pure. The pure crystallized compound can optionally include a crystallization solvent or solvents. If desired, a recrystallization process can be repeated one or more times to increase the purity of the diacetylenic compound, using the same or a different solvent system.

The invention also includes time-temperature indicators comprising a crystal phase containing a diacetylenic compound of structure

[CH$_3$(CH$_2$)$_n$NHCONH(CH$_2$)$_m$C≡C—]$_2$.

wherein "n" can be an odd number (integer) from 1 to 19 and "m" can be an odd number (integer) from 1 to 7. A first diacetylenic molecule of the diacetylenic compound can polymerize by reaction with diacetylene groups in two neighboring diacetylenic molecules. Also, the two =C=O groups on the first diacetylenic molecule can each hydrogen bond to two —NH— groups in a neighboring diacetylenic molecule. The crystal phase can be triclinic and optionally can have a center of symmetry.

In some embodiments of this time-temperature indicator, the triclinic crystal phase comprises two or more different diacetylenic compounds having the structure stated. In each diacetylenic molecule, "m" is an odd number. In one of the diacetylenic compounds "n" is an odd or even number having a first value and in another of the diacetylenic compounds "n" is also an odd or even number respectively and has a second value, the second value being a value different from the first value. In one embodiment of the invention, "n" is odd in both or all the diacetylenic compounds. In another embodiment "n" is even both or all the diacetylenic compounds. While the invention is not to be limited by any particular theory, it is believed that the zig-zag conformation often adopted by alkyl and alkylene groups may favor the described numerical selections of "m" and "n". Suitable examples of compounds having these structural characteristics will be, or become, apparent to a person of ordinary skill in the art in light of this disclosure.

The invention has been described largely with reference to diacetylenic compounds that are potentially useful for providing an appearance change in environmental monitors or indicators as a result of spontaneous polymerization under the monitored environmental condition or conditions. It will be understood that such useful properties are desirable in the products of the methods of the invention, but may not necessarily be possessed by the starting materials. Thus, it is contemplated that, in some cases, a diacetylenic compound having little, if any, useful indicator activity, in the raw state may be modified by a method or process of the invention to yield a product having useful indicator activity.

The invention also comprises any useful combination of two or more compatible ones of the various aspects, embodiments or features of the products and methods of the invention disclosed herein. A person of ordinary skill in the art will understand that many of the features or elements of the various embodiments and aspects of the invention disclosed herein can be used in combination one with another.

The entire disclosure of each and every United States patent and patent application, each foreign and international patent publication, of each other publication and of each unpublished patent application that is specifically referenced in this specification is hereby incorporated by reference herein, in its entirety.

The foregoing detailed description is to be read in light of and in combination with the preceding background and invention summary descriptions wherein partial or complete information regarding the best mode of practicing the invention, or regarding modifications, alternatives or useful embodiments of the invention may also be set forth or suggested, as will be apparent to one skilled in the art. Should there appear to be conflict between the meaning of a term as used in the written description of the invention in this specification and the usage in material incorporated by reference from another document, the meaning as used herein is intended to prevail.

Throughout the description, where compositions are described as having, including, or comprising specific components, or where processes are described as having, including, or comprising specific process steps, it is contemplated that compositions of the present invention can also consist essentially of, or consist of, the recited components, and that the processes of the present invention can also consist essentially of, or consist of, the recited processing steps. It should be understood that the order of steps or order for performing certain actions is immaterial so long as the invention remains operable. Moreover, two or more steps or actions may be conducted simultaneously. In addition, all proportions recited herein are to be understood to be proportions by weight, based upon the weight of the relevant composition, unless the context indicates otherwise.

While illustrative embodiments of the invention have been described above, it is, of course, understood that many and various modifications will be apparent to those of ordinary skill in the relevant art, or may become apparent as the art develops, in the light of the foregoing description. Such modifications are contemplated as being within the spirit and scope of the invention or inventions disclosed in this specification.

TABLE 9

Atomic coordinates (×10$^4$) and equivalent isotropic displacement parameters (Å$^2$ × 10$^3$) for KPr. U(eq) is defined as one third of the trace of the orthogonalized U$^{ij}$ tensor.

|      | x       | y       | z       | U(eq) |
|------|---------|---------|---------|-------|
| O(1) | 2882(1) | 7863(4) | 4898(2) | 41(1) |
| N(1) | 2476(1) | 3520(6) | 5799(3) | 41(1) |
| N(2) | 3450(1) | 3675(5) | 4292(3) | 40(1) |
| C(1) | 679(2)  | 6960(7) | 6386(4) | 52(1) |
| C(2) | 1276(2) | 5519(7) | 5517(4) | 46(1) |
| C(3) | 1899(1) | 4826(6) | 6607(3) | 40(1) |
| C(4) | 2930(1) | 5161(6) | 4986(3) | 36(1) |
| C(5) | 3909(1) | 5186(6) | 3219(4) | 38(1) |
| C(6) | 4388(2) | 7234(6) | 4019(4) | 38(1) |
| C(7) | 4780(2) | 9002(6) | 4634(4) | 38(1) |

TABLE 10

Bond lengths [Å] and angles [°] for KPr.

| O(1)—C(4)         | 1.247(3) |
| N(1)—C(4)         | 1.356(4) |
| N(1)—C(3)         | 1.446(4) |
| N(1)—H(1)         | 0.79(4)  |
| N(2)—C(4)         | 1.356(4) |
| N(2)—C(5)         | 1.460(4) |
| N(2)—H(2)         | 1.08(5)  |
| C(1)—C(2)         | 1.529(4) |
| C(1)—H(1A)        | 0.9800   |
| C(1)—H(1B)        | 0.9800   |
| C(1)—H(1C)        | 0.9800   |
| C(2)—C(3)         | 1.516(4) |
| C(2)—H(2A)        | 0.9900   |
| C(2)—H(2B)        | 0.9900   |
| C(3)—H(3A)        | 0.9900   |
| C(3)—H(3B)        | 0.9900   |
| C(5)—C(6)         | 1.463(4) |
| C(5)—H(5A)        | 0.9900   |
| C(5)—H(5B)        | 0.9900   |
| C(6)—C(7)         | 1.211(4) |
| C(7)—C(7)#1       | 1.377(6) |
| C(7)—C(6)#2       | 3.452(4) |
| C(4)—N(1)—C(3)    | 121.4(3) |
| C(4)—N(1)—H(1)    | 116(2)   |
| C(3)—N(1)—H(1)    | 122(2)   |
| C(4)—N(2)—C(5)    | 119.7(3) |
| C(4)—N(2)—H(2)    | 121(2)   |
| C(5)—N(2)—H(2)    | 117(2)   |
| C(2)—C(1)—H(1A)   | 109.5    |
| C(2)—C(1)—H(1B)   | 109.5    |
| H(1A)—C(1)—H(1B)  | 109.5    |
| C(2)—C(1)—H(1C)   | 109.5    |
| H(1A)—C(1)—H(1C)  | 109.5    |
| H(1B)—C(1)—H(1C)  | 109.5    |
| C(3)—C(2)—C(1)    | 112.4(3) |
| C(3)—C(2)—H(2A)   | 109.1    |
| C(1)—C(2)—H(2A)   | 109.1    |
| C(3)—C(2)—H(2B)   | 109.1    |
| C(1)—C(2)—H(2B)   | 109.1    |
| H(2A)—C(2)—H(2B)  | 107.9    |
| N(1)—C(3)—C(2)    | 113.2(2) |
| N(1)—C(3)—H(3A)   | 108.9    |
| C(2)—C(3)—H(3A)   | 108.9    |
| N(1)—C(3)—H(3B)   | 108.9    |
| C(2)—C(3)—H(3B)   | 108.9    |
| H(3A)—C(3)—H(3B)  | 107.8    |
| O(1)—C(4)—N(1)    | 122.5(3) |

TABLE 10-continued

Bond lengths [Å] and angles [°] for KPr.

| O(1)—C(4)—N(2)      | 121.9(3) |
| N(1)—C(4)—N(2)      | 115.6(3) |
| N(2)—C(5)—C(6)      | 113.3(2) |
| N(2)—C(5)—H(5A)     | 108.9    |
| C(6)—C(5)—H(5A)     | 108.9    |
| N(2)—C(5)—H(5B)     | 108.9    |
| C(6)—C(5)—H(5B)     | 108.9    |
| H(5A)—C(5)—H(5B)    | 107.7    |
| C(7)—C(6)—C(5)      | 177.5(3) |
| C(6)—C(7)—C(7)#1    | 178.7(4) |
| C(6)—C(7)—C(6)#2    | 81.8(2)  |
| C(7)#1—C(7)—C(6)#2  | 97.8(2)  |

Symmetry transformations used to generate equivalent atoms:
1 −x + 1, −y + 2, −z + 1
2 −x + 1, −y + 1, −z + 1

TABLE 11

Anisotropic displacement parameters (Å$^2$ × 10$^3$) for KPr. The anisotropic displacement factor exponent takes the form:
$-2\pi^2[h^2 a^{*2} U^{11} + \ldots + 2 h k a^* b^* U^{12}]$

|      | U$^{11}$ | U$^{22}$ | U$^{33}$ | U$^{23}$ | U$^{13}$ | U$^{12}$ |
|------|-------|-------|-------|-------|-------|-------|
| O(1) | 57(1) | 13(1) | 54(1) | −2(1) | 11(1) | 1(1)  |
| N(1) | 55(2) | 17(2) | 54(2) | 2(1)  | 16(1) | 2(1)  |
| N(2) | 54(2) | 19(1) | 47(2) | 0(1)  | 15(1) | 1(1)  |
| C(1) | 56(2) | 34(2) | 65(2) | −3(2) | 5(2)  | 3(1)  |
| C(2) | 57(2) | 32(2) | 50(2) | −3(2) | 13(2) | 2(1)  |
| C(3) | 55(2) | 21(2) | 43(2) | 1(2)  | 11(1) | 0(1)  |
| C(4) | 51(2) | 20(2) | 37(2) | −1(1) | 8(1)  | 1(1)  |
| C(5) | 50(2) | 17(2) | 48(2) | 0(1)  | 12(1) | −2(1) |
| C(6) | 49(2) | 19(2) | 47(2) | 4(1)  | 14(1) | 5(1)  |
| C(7) | 53(2) | 16(2) | 46(2) | 7(1)  | 11(1) | 3(1)  |

TABLE 12

Hydrogen coordinates (× 10$^4$) and isotropic displacement parameters (Å$^2$ × 10$^3$) for KPr.

|       | x        | y         | z        | U(eq)   |
|-------|----------|-----------|----------|---------|
| H(1)  | 2508(15) | 1810(90)  | 5700(40) | 53(11)  |
| H(2)  | 3449(19) | 1320(110) | 4260(50) | 96(13)  |
| H(1A) | 291      | 7383      | 5636     | 77      |
| H(1B) | 847      | 8777      | 6872     | 77      |
| H(1C) | 518      | 5644      | 7208     | 77      |
| H(2A) | 1102     | 3697      | 5018     | 55      |
| H(2B) | 1427     | 6833      | 4668     | 55      |
| H(3A) | 2064     | 6643      | 7125     | 47      |
| H(3B) | 1748     | 3481      | 7441     | 47      |
| H(5A) | 3617     | 6258      | 2425     | 46      |
| H(5B) | 4187     | 3727      | 2650     | 46      |

The invention claimed is:

1. Crystallized 2,4-hexadiyn-1,6-bis(ethylurea) having a crystal structure wherein the molecules have a center-to-center separation of less than 4.7 Å between the geometric centers of the diacetylene units in neighboring molecules in a direction wherein solid-state polymerization can occur.

2. Crystallized 2,4-hexadiyn-1,6-bis(ethylurea) according to claim 1 wherein the center-to-center separation corresponds to a unit cell repeat distance of the crystallized diacetylenic compound.

3. Crystallized 2,4-hexadiyn-1,6-bis(ethylurea) according to claim 1 having a triclinic crystal structure.

4. Crystallized 2,4-hexadiyn-1,6-bis(ethylurea) according to claim 1 having a triclinic crystal structure in space group P1(bar).

5. Crystallized 2,4-hexadiyn-1,6-bis(ethylurea) according to claim 1 comprising two hydrogen bonds to each urea group in the molecule, each one of the two hydrogen bonds extending between one of the two NH groups in a urea group in one molecule of 2,4-hexadiyn-1,6-bis(ethylurea) and a C=O group in a neighboring molecule of 2,4-hexadiyn-1,6-bis(ethylurea).

6. Crystallized 2,4-hexadiyn-1,6-bis(ethylurea) according to claim 5 having a triclinic crystal structure and a purity of at least about 98 percent by weight.

7. Crystallized 2,4-hexadiyn-1,6-bis(ethylurea) according to claim 1 wherein the center-to-center separation is 4.620 Å.

8. Crystallized 2,4-hexadiyn-1,6-bis(ethylurea) according to claim 1 having a crystal structure with unit cell parameters of a=4.248 Å, b=4.620 Å, c=16.558 Å, $60=88.97°$, $62=84.66°$ and $\gamma=81.41°$.

9. Crystallized 2,4-hexadiyn-1,6-bis(ethylurea) according to claim 8 having a centrosymmetric crystal structure.

10. Crystallized 2,4-hexadiyn-1,6-bis(ethylurea) according to claim 1 having a crystal size in a first direction of greater than about 100 micron and a maximum dimension in a second direction perpendicular to the first direction of not more than about 10 micron.

11. Crystallized 2,4-hexadiyn-1,6-bis(ethylurea) according to claim 1 comprising not more than 3 percent by weight of polymerized 2,4-hexadiyn-1,6-bis(ethylurea), based upon the weight of 2,4-hexadiyn-1,6-bis(ethylurea) and of the polymer.

12. Crystallized 2,4-hexadiyn-1,6-bis(propylurea) having a crystal structure wherein the molecules have a center-to-center separation of less than 4.7 Å between the geometric centers of the diacetylene units in neighboring molecules in a direction wherein solid-state polymerization can occur.

13. Crystallized 2,4-hexadiyn-1,6-bis(propylurea) according to claim 12 wherein the center-to-center separation corresponds to a unit cell repeat distance of the crystallized diacetylenic compound.

14. Crystallized 2,4-hexadiyn-1,6-bis(propylurea) according to claim 12 having a monoclinic crystal structure.

15. Crystallized 2,4-hexadiyn-1,6-bis(propylurea) according to claim 12 having a monoclinic crystal structure in space group $P2_1/a$.

16. Crystallized 2,4-hexadiyn-1,6-bis(propylurea) according to claim 12 comprising two hydrogen bonds to each urea group in the molecule, each one of the two hydrogen bonds extending between one of the two NH groups in a urea group in one molecule of 2,4-hexadiyn-1,6-bis(propylurea) and a C=O group in a neighboring molecule of 2,4-hexadiyn-1,6-bis(propylurea).

17. Crystallized 2,4-hexadiyn-1,6-bis(propylurea) according to claim 16 having a monoclinic crystal structure and a purity of at least about 98 percent by weight.

18. Crystallized 2,4-hexadiyn-1,6-bis(propylurea) according to claim 12 wherein the center-to-center separation is 4.594 Å.

19. Crystallized 2,4-hexadiyn-1,6-bis(propylurea) according to claim 12 having a crystal structure with unit cell parameters of a=8.447 Å, b=4.594 Å, c=19.10 Å, $\alpha=90°$ $\beta=91.960°$, and $\gamma=90°$.

20. Crystallized 2,4-hexadiyn-1,6-bis(propylurea) according to claim 12 comprising not more than 3 percent by weight of polymerized 2,4-hexadiyn-1,6-bis(propylurea), based upon the weight of 2,4-hexadiyn-1,6-bis(propylurea) and of the polymer.

* * * * *